United States Patent
Budde et al.

(10) Patent No.: US 10,571,477 B2
(45) Date of Patent: Feb. 25, 2020

(54) MARKER SEQUENCES FOR DIAGNOSING AND STRATIFYING SYSTEMIC SCLEROSIS PATIENTS

(71) Applicant: PROTAGEN AG, Dortmund (DE)

(72) Inventors: Petra Budde, Dortmund (DE); Peter Schulz-Knappe, Hemmingen (DE); Angelika Lüking, Bochum (DE); Martin Garner, Dortmund (DE)

(73) Assignee: Protagen GmbH, Dortmund (DE)

( * ) Notice: Subject to any disclaimer, the term of this patent is extended or adjusted under 35 U.S.C. 154(b) by 197 days.

(21) Appl. No.: 15/324,470

(22) PCT Filed: Jul. 4, 2015

(86) PCT No.: PCT/EP2015/065268
§ 371 (c)(1),
(2) Date: Jan. 6, 2017

(87) PCT Pub. No.: WO2016/005295
PCT Pub. Date: Jan. 14, 2016

(65) Prior Publication Data
US 2017/0199202 A1   Jul. 13, 2017

(30) Foreign Application Priority Data
Jul. 7, 2014 (EP) .................................. 14176035

(51) Int. Cl.
| | | |
|---|---|---|
| *G01N 33/68* | (2006.01) | |
| *G01N 33/564* | (2006.01) | |
| *C07K 16/18* | (2006.01) | |
| *C07K 14/47* | (2006.01) | |
| *C07K 16/40* | (2006.01) | |

(52) U.S. Cl.
CPC ......... *G01N 33/6893* (2013.01); *C07K 14/47* (2013.01); *C07K 16/18* (2013.01); *C07K 16/40* (2013.01); *G01N 33/564* (2013.01); *C07K 2317/33* (2013.01); *C07K 2317/34* (2013.01); *G01N 2500/04* (2013.01); *G01N 2800/24* (2013.01); *G01N 2800/52* (2013.01)

(58) Field of Classification Search
None
See application file for complete search history.

(56) References Cited

FOREIGN PATENT DOCUMENTS

| WO | WO-2010/045388 A2 | 4/2010 |
|---|---|---|
| WO | WO-2015/169973 A2 | 11/2015 |

OTHER PUBLICATIONS

Rizou, C., et al., "B-Cell Epitope Mapping of DNA Topoisomerase I Defines Epitopes Strongly Associated with Pulmonary Fibrosis in Systemic Sclerosis", Am. J. Respir. Cell Mol. Biol., 2000, vol. 22, No. 3, pp. 344-351.

Hecker, M., et al., "Computational Analysis of High-Density Peptide Microarray Data with Application from Systemic Sclerosis to Multiple Sclerosis", Autoimmun. Rev., 2012, vol. 11, No. 3, pp. 180-190.

International Search Report for PCT/EP2015/065268 dated Dec. 18, 2015 with English Translation Thereof Attached.

Written Opinion of the International Searching Authority for PCT/EP2015/065268 dated Dec. 18, 2015.

International Preliminary Report on Patentability for PCT/EP2015/065268 dated Jan. 10, 2017 with English Translation Thereof Attached.

*Primary Examiner* — Changhwa J Cheu

(74) *Attorney, Agent, or Firm* — Finnegan, Henderson, Farabow, Garrett and Dunner, LLP

(57) ABSTRACT

The present invention relates to methods for identifying markers for systemic sclerosis (also scleroderma; SSc) and to the markers identified with the aid of this method, which can differentiate between SSc and other autoimmune diseases on the one hand and between different SSc subgroups on the other hand. The invention also relates to panels, diagnostic devices and test kits which comprise these markers, and to the use and application thereof, for example for the diagnosis, prognosis and therapy control of SSc. The invention also relates to methods for screening and for validating active substances for use in SSc.

11 Claims, 4 Drawing Sheets

Specification includes a Sequence Listing.

```
                       SEQUENCE LISTING

<160> NUMBER OF SEQ ID NOS: 120

<210> SEQ ID NO 1
    <211> LENGTH: 30
    <212> TYPE: PRT
    <213> ORGANISM: Homo sapiens

<400> SEQUENCE: 1

Ser Pro Gln Pro Ser Ala Ser Ser Ser Gln Phe Ser Thr Ser Gly
    1               5                   10                  15
```

Gly Pro Trp Ala Arg Glu Arg Arg Ala Gly Glu Glu Pro Val
            20                  25                  30

<210> SEQ ID NO 2
<211> LENGTH: 12
<212> TYPE: PRT
<213> ORGANISM: Homo sapiens

<400> SEQUENCE: 2

Leu Pro Ala Pro Leu Pro Pro Ser His Gly Ser Ser
1               5                   10

<210> SEQ ID NO 3
<211> LENGTH: 12
<212> TYPE: PRT
<213> ORGANISM: Homo sapiens

<400> SEQUENCE: 3

Ser Pro Gln Pro Ser Ala Ser Ser Ser Gln Phe
1               5                   10

<210> SEQ ID NO 4
<211> LENGTH: 13
<212> TYPE: PRT
<213> ORGANISM: Homo sapiens

<400> SEQUENCE: 4

Ser Ser Gln Phe Ser Thr Ser Gly Gly Pro Trp Ala Arg
1               5                   10

<210> SEQ ID NO 5
<211> LENGTH: 13
<212> TYPE: PRT
<213> ORGANISM: Homo sapiens

<400> SEQUENCE: 5

Arg Glu Lys Leu Asn Pro Pro Thr Pro Ser Ile Tyr Leu
1               5                   10

<210> SEQ ID NO 6
<211> LENGTH: 15
<212> TYPE: PRT
<213> ORGANISM: Homo sapiens

<400> SEQUENCE: 6

Gly Gly Pro Trp Ala Arg Glu Arg Arg Ala Gly Glu Glu Pro Val
1               5                   10                  15

<210> SEQ ID NO 7
<211> LENGTH: 14
<212> TYPE: PRT
<213> ORGANISM: Homo sapiens

<400> SEQUENCE: 7

Pro Arg Glu Lys Leu Asn Pro Pro Thr Pro Ser Ile Tyr Leu
1               5                   10

<210> SEQ ID NO 8
<211> LENGTH: 15
<212> TYPE: PRT
<213> ORGANISM: Homo sapiens

<400> SEQUENCE: 8

Tyr Gln Tyr Gln Leu Ala Leu Glu Arg Tyr Glu Trp Asn Glu Val
1               5                   10                  15

<210> SEQ ID NO 9
<211> LENGTH: 34
<212> TYPE: PRT
<213> ORGANISM: Homo sapiens

<400> SEQUENCE: 9

Pro Arg Arg Arg Ser Arg Lys Pro Glu Ala Pro Arg Arg Ser Pro
1               5                   10                  15

Ser Pro Thr Pro Thr Pro Gly Pro Ser Arg Arg Gly Pro Ser Leu Gly
            20                  25                  30

Ala Ser

<210> SEQ ID NO 10
<211> LENGTH: 12
<212> TYPE: PRT
<213> ORGANISM: Homo sapiens

<400> SEQUENCE: 10

Ser Pro Ser Pro Thr Pro Thr Pro Gly Pro Ser Arg
1               5                   10

<210> SEQ ID NO 11
<211> LENGTH: 12
<212> TYPE: PRT
<213> ORGANISM: Homo sapiens

<400> SEQUENCE: 11

Gly Pro Ser Arg Arg Gly Pro Ser Leu Gly Ala Ser
1               5                   10

<210> SEQ ID NO 12
<211> LENGTH: 12
<212> TYPE: PRT
<213> ORGANISM: Homo sapiens

<400> SEQUENCE: 12

Thr Pro Thr Pro Gly Pro Ser Arg Arg Gly Pro Ser
1               5                   10

<210> SEQ ID NO 13
<211> LENGTH: 13
<212> TYPE: PRT
<213> ORGANISM: Homo sapiens

<400> SEQUENCE: 13

Arg Ser Pro Ser Pro Thr Pro Thr Pro Gly Pro Ser Arg
1               5                   10

<210> SEQ ID NO 14
<211> LENGTH: 12
<212> TYPE: PRT
<213> ORGANISM: Homo sapiens

<400> SEQUENCE: 14

Pro Arg Arg Arg Ser Arg Lys Pro Glu Ala Pro Arg
1               5                   10

<210> SEQ ID NO 15
<211> LENGTH: 13
<212> TYPE: PRT
<213> ORGANISM: Homo sapiens

<400> SEQUENCE: 15

```
Arg Ser Pro Ser Pro Thr Pro Thr Pro Gly Pro Ser Arg
1               5                   10
```

<210> SEQ ID NO 16
<211> LENGTH: 15
<212> TYPE: PRT
<213> ORGANISM: Homo sapiens

<400> SEQUENCE: 16

```
Ala Pro Arg Arg Arg Ser Pro Ser Pro Thr Pro Thr Pro Gly Pro
1               5                   10                  15
```

<210> SEQ ID NO 17
<211> LENGTH: 15
<212> TYPE: PRT
<213> ORGANISM: Homo sapiens

<400> SEQUENCE: 17

```
Arg Arg Arg Ser Pro Ser Pro Thr Pro Thr Pro Gly Pro Ser Arg
1               5                   10                  15
```

<210> SEQ ID NO 18
<211> LENGTH: 15
<212> TYPE: PRT
<213> ORGANISM: Homo sapiens

<400> SEQUENCE: 18

```
Ser Pro Ser Pro Thr Pro Thr Pro Gly Pro Ser Arg Arg Gly Pro
1               5                   10                  15
```

<210> SEQ ID NO 19
<211> LENGTH: 15
<212> TYPE: PRT
<213> ORGANISM: Homo sapiens

<400> SEQUENCE: 19

```
Lys Arg Asn Tyr Gly Ala Lys Arg Gly Gly Pro Pro Val Lys Arg
1               5                   10                  15
```

<210> SEQ ID NO 20
<211> LENGTH: 15
<212> TYPE: PRT
<213> ORGANISM: Homo sapiens

<400> SEQUENCE: 20

```
Phe Pro Lys Thr Pro Glu Val Gly Pro Gly Pro Pro Gly Pro
1               5                   10                  15
```

<210> SEQ ID NO 21
<211> LENGTH: 15
<212> TYPE: PRT
<213> ORGANISM: Homo sapiens

<400> SEQUENCE: 21

```
Gly His Pro Ser Lys Pro Tyr Tyr Ala Pro Gly Ala Pro Thr Pro
1               5                   10                  15
```

<210> SEQ ID NO 22
<211> LENGTH: 140
<212> TYPE: PRT
<213> ORGANISM: Homo sapiens

<400> SEQUENCE: 22

```
Met Gly Pro Arg Arg Arg Ser Arg Lys Pro Glu Ala Pro Arg Arg Arg
```

```
  1               5                  10                 15
Ser Pro Ser Pro Thr Pro Thr Pro Gly Pro Ser Arg Arg Gly Pro Ser
            20                 25                 30

Leu Gly Ala Ser Ser His Gln His Ser Arg Arg Gln Gly Trp Leu
            35                 40                 45

Lys Glu Ile Arg Lys Leu Gln Lys Ser Thr His Leu Leu Ile Arg Lys
 50                  55                 60

Leu Pro Phe Ser Arg Leu Ala Arg Glu Ile Cys Val Lys Phe Thr Arg
 65                  70                 75                 80

Gly Val Asp Phe Asn Trp Gln Ala Gln Ala Leu Leu Ala Leu Gln Glu
                 85                 90                 95

Ala Ala Glu Ala Phe Leu Val His Leu Phe Glu Asp Ala Tyr Leu Leu
            100                105                110

Thr Leu His Ala Gly Arg Val Thr Leu Phe Pro Lys Asp Val Gln Leu
            115                120                125

Ala Arg Arg Ile Arg Gly Leu Glu Glu Gly Leu Gly
            130                135                140
```

<210> SEQ ID NO 23
<211> LENGTH: 1431
<212> TYPE: DNA
<213> ORGANISM: Homo sapiens

<400> SEQUENCE: 23

```
ccgtgaagtg ggcggagcga gcgatttgaa cgcgagcggc gcggacttct gccaagcacc      60
ggctcatgtg aggctcgcgg cacagcgttc tctgggctcc ccagaagcca gcctttcgct     120
cccggacccg gcagcccgag caggagccgt gggaccgggc gccagcaccc tctgcggcgt     180
gtcatgggcc cgcgccgccg gagccgaaag cccgaggccc cgaggaggcg cagcccgagc     240
ccgaccccga ccccggccc ctcccggcgg ggcccctcct taggcgcttc ctcccatcaa      300
cacagtcggc ggagacaagg ttggctaaag gagatccgaa agcttcagaa gagcacacac     360
ctcttgataa ggaagctgcc cttcagccgc ctggcaagag aaatatgtgt taaattcact     420
cgtggtgtgg acttcaattg gcaagcccag gccctattgg ccctacaaga ggcagcagaa     480
gcatttctag ttcatctctt tgaggacgcc tatctcctca ccttacatgc aggccgagtt     540
actctcttcc caaggatgt gcaactggcc cggaggatcc ggggccttga ggagggactc     600
ggctgagctc ctgcacccag tgtttctgtc agtctttcct gctcagccag ggggatgat     660
accggggact ctccagagcc atgactagat ccaatggatt ctgcgatgct gtctggactt     720
tgctgtctct gaacagtatg tgtgtgttgc tttaaatatt tttctttttt ttgagaagga     780
gaagactgca tgactttcct ctgtaacaga ggtaatatat gagacaatca acaccgttcc     840
aaaggcctga aaataatttt cagataaaga gactccaagg ttgactttag tttgtgagtt     900
actcatgtga ctatttgagg attttgaaaa catcagattt gctgtggtat gggagaaaag     960
gctatgtact tattatttta gctctttctg taatatttac attttttacc atatgtacat    1020
ttgtactttt attttacaca taagggaaaa aataagacca ctttgagcag ttgcctggaa    1080
ggctgggcat ttccatcata tagacctctg cccttcagag tagcctcacc attagtggca    1140
gcatcatgta actgagtgga ctgtgcttgt caacggatgt gtagcttttc agaaacttaa    1200
ttggggatga atagaaaacc tgtaagcttt gatgttctgg ttacttctag taaattcctg    1260
tcaaaatcaa ttcagaaatt ctaacttgga gaatttaaca ttttactctt gtaaatcata    1320
gaagatgtat cataacagtt cagaattttta aagtacattt tcgatgcttt tatgggtatt    1380
```
tttgtagttt ctttgtagag agataataaa aatcaaaata tttaatgaaa a         1431

<210> SEQ ID NO 24
<211> LENGTH: 1682
<212> TYPE: PRT
<213> ORGANISM: Homo sapiens

<400> SEQUENCE: 24

Met His Arg Ala Val Asp Pro Pro Gly Ala Arg Ala Arg Glu Ala
1               5                   10                  15

Phe Ala Leu Gly Gly Leu Ser Cys Ala Gly Ala Trp Ser Ser Cys Pro
            20                  25                  30

Pro His Pro Pro Arg Ser Ala Trp Leu Pro Gly Gly Arg Cys Ser
        35                  40                  45

Ala Ser Ile Gly Gln Pro Pro Leu Pro Ala Pro Leu Pro Pro Ser His
50                  55                  60

Gly Ser Ser Gly His Pro Ser Lys Pro Tyr Tyr Ala Pro Gly Ala
65                  70                  75                  80

Pro Thr Pro Arg Pro Leu His Gly Lys Leu Glu Ser Leu His Gly Cys
                85                  90                  95

Val Gln Ala Leu Leu Arg Glu Pro Ala Gln Pro Gly Leu Trp Glu Gln
            100                 105                 110

Leu Gly Gln Leu Tyr Glu Ser Glu His Asp Ser Glu Glu Ala Thr Arg
        115                 120                 125

Cys Tyr His Ser Ala Leu Arg Tyr Gly Gly Ser Phe Ala Glu Leu Gly
    130                 135                 140

Pro Arg Ile Gly Arg Leu Gln Gln Ala Gln Leu Trp Asn Phe His Thr
145                 150                 155                 160

Gly Ser Cys Gln His Arg Ala Lys Val Leu Pro Pro Leu Glu Gln Val
                165                 170                 175

Trp Asn Leu Leu His Leu Glu His Lys Arg Asn Tyr Gly Ala Lys Arg
            180                 185                 190

Gly Gly Pro Pro Val Lys Arg Ala Ala Glu Pro Pro Val Val Gln Pro
        195                 200                 205

Val Pro Pro Ala Ala Leu Ser Gly Pro Ser Gly Glu Glu Gly Leu Ser
    210                 215                 220

Pro Gly Gly Lys Arg Arg Arg Gly Cys Asn Ser Glu Gln Thr Gly Leu
225                 230                 235                 240

Pro Pro Gly Leu Pro Leu Pro Pro Pro Leu Pro Pro Pro Pro
                245                 250                 255

Pro Pro Pro Pro Pro Pro Pro Leu Pro Gly Leu Ala Thr Ser Pro
            260                 265                 270

Pro Phe Gln Leu Thr Lys Pro Gly Leu Trp Ser Thr Leu His Gly Asp
        275                 280                 285

Ala Trp Gly Pro Glu Arg Lys Gly Ser Ala Pro Pro Glu Arg Gln Glu
    290                 295                 300

Gln Arg His Ser Leu Pro His Pro Tyr Pro Tyr Pro Ala Pro Ala Tyr
305                 310                 315                 320

Thr Ala His Pro Pro Gly His Arg Leu Val Pro Ala Pro Pro Gly
                325                 330                 335

Pro Gly Pro Arg Pro Pro Gly Ala Glu Ser His Gly Cys Leu Pro Ala
            340                 345                 350

Thr Arg Pro Pro Gly Ser Asp Leu Arg Glu Ser Arg Val Gln Arg Ser
        355                 360                 365

```
Arg Met Asp Ser Ser Val Ser Pro Ala Ala Thr Thr Ala Cys Val Pro
    370             375             380
Tyr Ala Pro Ser Arg Pro Pro Gly Leu Pro Gly Thr Thr Thr Ser Ser
385             390             395             400
Ser Ser Ser Ser Ser Ser Asn Thr Gly Leu Arg Gly Val Glu Pro Asn
            405             410             415
Pro Gly Ile Pro Gly Ala Asp His Tyr Gln Thr Pro Ala Leu Glu Val
        420             425             430
Ser His His Gly Arg Leu Gly Pro Ser Ala His Ser Ser Arg Lys Pro
        435             440             445
Phe Leu Gly Ala Pro Ala Ala Thr Pro His Leu Ser Leu Pro Pro Gly
    450             455             460
Pro Ser Ser Pro Pro Pro Pro Cys Pro Arg Leu Leu Arg Pro Pro
465             470             475             480
Pro Pro Pro Ala Trp Leu Lys Gly Pro Ala Cys Arg Ala Ala Arg Glu
            485             490             495
Asp Gly Glu Ile Leu Glu Glu Leu Phe Phe Gly Thr Glu Gly Pro Pro
        500             505             510
Arg Pro Ala Pro Pro Leu Pro His Arg Glu Gly Phe Leu Gly Pro
    515             520             525
Pro Ala Ser Arg Phe Ser Val Gly Thr Gln Asp Ser His Thr Pro Pro
    530             535             540
Thr Pro Pro Thr Pro Thr Thr Ser Ser Ser Asn Ser Asn Ser Gly Ser
545             550             555             560
His Ser Ser Ser Pro Ala Gly Pro Val Ser Phe Pro Pro Pro Tyr
            565             570             575
Leu Ala Arg Ser Ile Asp Pro Leu Pro Arg Pro Pro Ser Pro Ala Gln
            580             585             590
Asn Pro Gln Asp Pro Pro Leu Val Pro Leu Thr Leu Ala Leu Pro Pro
        595             600             605
Ala Pro Pro Ser Ser Cys His Gln Asn Thr Ser Gly Ser Phe Arg Arg
        610             615             620
Pro Glu Ser Pro Arg Pro Arg Val Ser Phe Pro Lys Thr Pro Glu Val
625             630             635             640
Gly Pro Gly Pro Pro Gly Pro Leu Ser Lys Ala Pro Gln Pro Val
            645             650             655
Pro Pro Gly Val Gly Glu Leu Pro Ala Arg Gly Pro Arg Leu Phe Asp
            660             665             670
Phe Pro Pro Thr Pro Leu Glu Asp Gln Phe Glu Glu Pro Ala Glu Phe
        675             680             685
Lys Ile Leu Pro Asp Gly Leu Ala Asn Ile Met Lys Met Leu Asp Glu
        690             695             700
Ser Ile Arg Lys Glu Glu Glu Gln Gln His Glu Ala Gly Val Ala
705             710             715             720
Pro Gln Pro Pro Leu Lys Glu Pro Phe Ala Ser Leu Gln Ser Pro Phe
            725             730             735
Pro Thr Asp Thr Ala Pro Thr Thr Thr Ala Pro Ala Val Ala Val Thr
        740             745             750
Thr Thr Thr Thr Thr Thr Thr Thr Thr Ala Thr Gln Glu Glu Glu
        755             760             765
Lys Lys Pro Pro Pro Ala Leu Pro Pro Pro Pro Leu Ala Lys Phe
770             775             780
```

-continued

```
Pro Pro Pro Ser Gln Pro Gln Pro Pro Pro Pro Pro Ser Pro
785                 790             795             800

Ala Ser Leu Leu Lys Ser Leu Ala Ser Val Leu Glu Gly Gln Lys Tyr
            805                 810             815

Cys Tyr Arg Gly Thr Gly Ala Ala Val Ser Thr Arg Pro Gly Pro Leu
            820                 825             830

Pro Thr Thr Gln Tyr Ser Pro Gly Pro Pro Ser Gly Ala Thr Ala Leu
            835                 840             845

Pro Pro Thr Ser Ala Ala Pro Ser Ala Gln Gly Ser Pro Gln Pro Ser
850                 855             860

Ala Ser Ser Ser Gln Phe Ser Thr Ser Gly Gly Pro Trp Ala Arg
865                 870             875             880

Glu Arg Arg Ala Gly Glu Glu Pro Val Pro Gly Pro Met Thr Pro Thr
                885                 890             895

Gln Pro Pro Pro Leu Ser Leu Pro Pro Ala Arg Ser Glu Ser Glu
                900             905             910

Val Leu Glu Glu Ile Ser Arg Ala Cys Glu Thr Leu Val Glu Arg Val
            915                 920             925

Gly Arg Ser Ala Thr Asp Pro Ala Asp Pro Val Asp Thr Ala Glu Pro
930                 935             940

Ala Asp Ser Gly Thr Glu Arg Leu Leu Pro Pro Ala Gln Ala Lys Glu
945                 950             955             960

Glu Ala Gly Gly Val Ala Ala Val Ser Gly Ser Cys Lys Arg Arg Gln
                965                 970             975

Lys Glu His Gln Lys Glu His Arg Arg His Arg Ala Cys Lys Asp
            980                 985             990

Ser Val Gly Arg Arg Pro Arg Glu  Gly Arg Ala Lys Ala  Lys Ala Lys
            995                1000            1005

Val Pro  Lys Glu Lys Ser Arg  Arg Val Leu Gly Asn  Leu Asp Leu
    1010            1015            1020

Gln Ser  Glu Glu Ile Gln Gly  Arg Glu Lys Ser Arg  Pro Asp Leu
    1025            1030            1035

Gly Gly  Ala Ser Lys Ala Lys  Pro Pro Thr Ala Pro  Ala Pro Pro
    1040            1045            1050

Ser Ala  Pro Ala Pro Ser Ala  Gln Pro Thr Pro  Ser Ala Ser
    1055            1060            1065

Val Pro  Gly Lys Lys Ala Arg  Glu Glu Ala Pro Gly  Pro Pro Gly
    1070            1075            1080

Val Ser  Arg Ala Asp Met Leu  Lys Leu Arg Ser Leu  Ser Glu Gly
    1085            1090            1095

Pro Pro  Lys Glu Leu Lys Ile  Arg Leu Ile Lys Val  Glu Ser Gly
    1100            1105            1110

Asp Lys  Glu Thr Phe Ile Ala  Ser Glu Val Glu Glu  Arg Arg Leu
    1115            1120            1125

Arg Met  Ala Asp Leu Thr Ile  Ser His Cys Ala Ala  Asp Val Val
    1130            1135            1140

Arg Ala  Ser Arg Asn Ala Lys  Val Lys Gly Lys Phe  Arg Glu Ser
    1145            1150            1155

Tyr Leu  Ser Pro Ala Gln Ser  Val Lys Pro Lys Ile  Asn Thr Glu
    1160            1165            1170

Glu Lys  Leu Pro Arg Glu Lys  Leu Asn Pro Pro Thr  Pro Ser Ile
    1175            1180            1185

Tyr Leu  Glu Ser Lys Arg Asp  Ala Phe Ser Pro Val  Leu Leu Gln
```

-continued

```
            1190                1195                1200
Phe Cys Thr Asp Pro Arg Asn Pro Ile Thr Val Ile Arg Gly Leu
            1205                1210                1215
Ala Gly Ser Leu Arg Leu Asn Leu Gly Leu Phe Ser Thr Lys Thr
            1220                1225                1230
Leu Val Glu Ala Ser Gly Glu His Thr Val Glu Val Arg Thr Gln
            1235                1240                1245
Val Gln Gln Pro Ser Asp Glu Asn Trp Asp Leu Thr Gly Thr Arg
            1250                1255                1260
Gln Ile Trp Pro Cys Glu Ser Ser Arg Ser His Thr Thr Ile Ala
            1265                1270                1275
Lys Tyr Ala Gln Tyr Gln Ala Ser Ser Phe Gln Glu Ser Leu Gln
            1280                1285                1290
Glu Glu Lys Glu Ser Glu Asp Glu Glu Ser Glu Glu Pro Asp Ser
            1295                1300                1305
Thr Thr Gly Thr Pro Pro Ser Ser Ala Pro Asp Pro Lys Asn His
            1310                1315                1320
His Ile Ile Lys Phe Gly Thr Asn Ile Asp Leu Ser Asp Ala Lys
            1325                1330                1335
Arg Trp Lys Pro Gln Leu Gln Glu Leu Leu Lys Leu Pro Ala Phe
            1340                1345                1350
Met Arg Val Thr Ser Thr Gly Asn Met Leu Ser His Val Gly His
            1355                1360                1365
Thr Ile Leu Gly Met Asn Thr Val Gln Leu Tyr Met Lys Val Pro
            1370                1375                1380
Gly Ser Arg Thr Pro Gly His Gln Glu Asn Asn Asn Phe Cys Ser
            1385                1390                1395
Val Asn Ile Asn Ile Gly Pro Gly Asp Cys Glu Trp Phe Ala Val
            1400                1405                1410
His Glu His Tyr Trp Glu Thr Ile Ser Ala Phe Cys Asp Arg His
            1415                1420                1425
Gly Val Asp Tyr Leu Thr Gly Ser Trp Trp Pro Ile Leu Asp Asp
            1430                1435                1440
Leu Tyr Ala Ser Asn Ile Pro Val Tyr Arg Phe Val Gln Arg Pro
            1445                1450                1455
Gly Asp Leu Val Trp Ile Asn Ala Gly Thr Val His Trp Val Gln
            1460                1465                1470
Ala Thr Gly Trp Cys Asn Asn Ile Ala Trp Asn Val Gly Pro Leu
            1475                1480                1485
Thr Ala Tyr Gln Tyr Gln Leu Ala Leu Glu Arg Tyr Glu Trp Asn
            1490                1495                1500
Glu Val Lys Asn Val Lys Ser Ile Val Pro Met Ile His Val Ser
            1505                1510                1515
Trp Asn Val Ala Arg Thr Val Lys Ile Ser Asp Pro Asp Leu Phe
            1520                1525                1530
Lys Met Ile Lys Phe Cys Leu Leu Gln Ser Met Lys His Cys Gln
            1535                1540                1545
Val Gln Arg Glu Ser Leu Val Arg Ala Gly Lys Lys Ile Ala Tyr
            1550                1555                1560
Gln Gly Arg Val Lys Asp Glu Pro Ala Tyr Tyr Cys Asn Glu Cys
            1565                1570                1575
Asp Val Glu Val Phe Asn Ile Leu Phe Val Thr Ser Glu Asn Gly
            1580                1585                1590
```

```
Ser Arg Asn Thr Tyr Leu Val His Cys Glu Gly Cys Ala Arg Arg
    1595                1600                1605

Arg Ser Ala Gly Leu Gln Gly Val Val Val Leu Glu Gln Tyr Arg
    1610                1615                1620

Thr Glu Glu Leu Ala Gln Ala Tyr Asp Ala Phe Thr Leu Val Arg
    1625                1630                1635

Ala Arg Arg Ala Arg Gly Gln Arg Arg Ala Leu Gly Gln Ala
    1640                1645                1650

Ala Gly Thr Gly Phe Gly Ser Pro Ala Ala Pro Phe Pro Glu Pro
    1655                1660                1665

Pro Pro Ala Phe Ser Pro Gln Ala Pro Ala Ser Thr Ser Arg
    1670                1675                1680

<210> SEQ ID NO 25
<211> LENGTH: 15
<212> TYPE: PRT
<213> ORGANISM: Homo sapiens

<400> SEQUENCE: 25

Gly Ser Gly Ser Gly Ser Gly Met Gly Pro Arg Arg Ser Arg
1               5                   10                  15

<210> SEQ ID NO 26
<211> LENGTH: 15
<212> TYPE: PRT
<213> ORGANISM: Homo sapiens

<400> SEQUENCE: 26

Ser Gly Ser Gly Met Gly Pro Arg Arg Ser Arg Lys Pro Glu
1               5                   10                  15

<210> SEQ ID NO 27
<211> LENGTH: 15
<212> TYPE: PRT
<213> ORGANISM: Homo sapiens

<400> SEQUENCE: 27

Gly Met Gly Pro Arg Arg Arg Ser Arg Lys Pro Glu Ala Pro Arg
1               5                   10                  15

<210> SEQ ID NO 28
<211> LENGTH: 15
<212> TYPE: PRT
<213> ORGANISM: Homo sapiens

<400> SEQUENCE: 28

Pro Arg Arg Arg Ser Arg Lys Pro Glu Ala Pro Arg Arg Ser
1               5                   10                  15

<210> SEQ ID NO 29
<211> LENGTH: 15
<212> TYPE: PRT
<213> ORGANISM: Homo sapiens

<400> SEQUENCE: 29

Arg Ser Arg Lys Pro Glu Ala Pro Arg Arg Ser Pro Ser Pro
1               5                   10                  15

<210> SEQ ID NO 30
<211> LENGTH: 15
<212> TYPE: PRT
<213> ORGANISM: Homo sapiens
```

<400> SEQUENCE: 30

Lys Pro Glu Ala Pro Arg Arg Ser Pro Ser Pro Thr Pro Thr
1               5                   10                  15

<210> SEQ ID NO 31
<211> LENGTH: 15
<212> TYPE: PRT
<213> ORGANISM: Homo sapiens

<400> SEQUENCE: 31

Ala Pro Arg Arg Arg Ser Pro Ser Pro Thr Pro Thr Pro Gly Pro
1               5                   10                  15

<210> SEQ ID NO 32
<211> LENGTH: 15
<212> TYPE: PRT
<213> ORGANISM: Homo sapiens

<400> SEQUENCE: 32

Arg Arg Ser Pro Ser Pro Thr Pro Thr Pro Gly Pro Ser Arg Arg
1               5                   10                  15

<210> SEQ ID NO 33
<211> LENGTH: 15
<212> TYPE: PRT
<213> ORGANISM: Homo sapiens

<400> SEQUENCE: 33

Pro Ser Pro Thr Pro Thr Pro Gly Pro Ser Arg Arg Gly Pro Ser
1               5                   10                  15

<210> SEQ ID NO 34
<211> LENGTH: 15
<212> TYPE: PRT
<213> ORGANISM: Homo sapiens

<400> SEQUENCE: 34

Thr Pro Thr Pro Gly Pro Ser Arg Arg Gly Pro Ser Leu Gly Ala
1               5                   10                  15

<210> SEQ ID NO 35
<211> LENGTH: 15
<212> TYPE: PRT
<213> ORGANISM: Homo sapiens

<400> SEQUENCE: 35

Pro Gly Pro Ser Arg Arg Gly Pro Ser Leu Gly Ala Ser Ser His
1               5                   10                  15

<210> SEQ ID NO 36
<211> LENGTH: 15
<212> TYPE: PRT
<213> ORGANISM: Homo sapiens

<400> SEQUENCE: 36

Ser Arg Arg Gly Pro Ser Leu Gly Ala Ser Ser His Gln His Ser
1               5                   10                  15

<210> SEQ ID NO 37
<211> LENGTH: 15
<212> TYPE: PRT
<213> ORGANISM: Homo sapiens

<400> SEQUENCE: 37

```
Gly Pro Ser Leu Gly Ala Ser Ser His Gln His Ser Arg Arg Arg
1               5                   10                  15

<210> SEQ ID NO 38
<211> LENGTH: 15
<212> TYPE: PRT
<213> ORGANISM: Homo sapiens

<400> SEQUENCE: 38

Leu Gly Ala Ser Ser His Gln His Ser Arg Arg Arg Gln Gly Trp
1               5                   10                  15

<210> SEQ ID NO 39
<211> LENGTH: 15
<212> TYPE: PRT
<213> ORGANISM: Homo sapiens

<400> SEQUENCE: 39

Ser Ser His Gln His Ser Arg Arg Arg Gln Gly Trp Leu Lys Glu
1               5                   10                  15

<210> SEQ ID NO 40
<211> LENGTH: 15
<212> TYPE: PRT
<213> ORGANISM: Homo sapiens

<400> SEQUENCE: 40

Gln His Ser Arg Arg Arg Gln Gly Trp Leu Lys Glu Ile Arg Lys
1               5                   10                  15

<210> SEQ ID NO 41
<211> LENGTH: 15
<212> TYPE: PRT
<213> ORGANISM: Homo sapiens

<400> SEQUENCE: 41

Arg Arg Arg Gln Gly Trp Leu Lys Glu Ile Arg Lys Leu Gln Lys
1               5                   10                  15

<210> SEQ ID NO 42
<211> LENGTH: 15
<212> TYPE: PRT
<213> ORGANISM: Homo sapiens

<400> SEQUENCE: 42

Gln Gly Trp Leu Lys Glu Ile Arg Lys Leu Gln Lys Ser Thr His
1               5                   10                  15

<210> SEQ ID NO 43
<211> LENGTH: 15
<212> TYPE: PRT
<213> ORGANISM: Homo sapiens

<400> SEQUENCE: 43

Leu Lys Glu Ile Arg Lys Leu Gln Lys Ser Thr His Leu Leu Ile
1               5                   10                  15

<210> SEQ ID NO 44
<211> LENGTH: 15
<212> TYPE: PRT
<213> ORGANISM: Homo sapiens

<400> SEQUENCE: 44

Ile Arg Lys Leu Gln Lys Ser Thr His Leu Leu Ile Arg Lys Leu
```

<210> SEQ ID NO 45
<211> LENGTH: 15
<212> TYPE: PRT
<213> ORGANISM: Homo sapiens

<400> SEQUENCE: 45

Leu Gln Lys Ser Thr His Leu Leu Ile Arg Lys Leu Pro Phe Ser
1               5                   10                  15

<210> SEQ ID NO 46
<211> LENGTH: 15
<212> TYPE: PRT
<213> ORGANISM: Homo sapiens

<400> SEQUENCE: 46

Ser Thr His Leu Leu Ile Arg Lys Leu Pro Phe Ser Arg Leu Ala
1               5                   10                  15

<210> SEQ ID NO 47
<211> LENGTH: 15
<212> TYPE: PRT
<213> ORGANISM: Homo sapiens

<400> SEQUENCE: 47

Leu Leu Ile Arg Lys Leu Pro Phe Ser Arg Leu Ala Arg Glu Ile
1               5                   10                  15

<210> SEQ ID NO 48
<211> LENGTH: 15
<212> TYPE: PRT
<213> ORGANISM: Homo sapiens

<400> SEQUENCE: 48

Arg Lys Leu Pro Phe Ser Arg Leu Ala Arg Glu Ile Cys Val Lys
1               5                   10                  15

<210> SEQ ID NO 49
<211> LENGTH: 15
<212> TYPE: PRT
<213> ORGANISM: Homo sapiens

<400> SEQUENCE: 49

Pro Phe Ser Arg Leu Ala Arg Glu Ile Cys Val Lys Phe Thr Arg
1               5                   10                  15

<210> SEQ ID NO 50
<211> LENGTH: 15
<212> TYPE: PRT
<213> ORGANISM: Homo sapiens

<400> SEQUENCE: 50

Arg Leu Ala Arg Glu Ile Cys Val Lys Phe Thr Arg Gly Val Asp
1               5                   10                  15

<210> SEQ ID NO 51
<211> LENGTH: 15
<212> TYPE: PRT
<213> ORGANISM: Homo sapiens

<400> SEQUENCE: 51

Arg Glu Ile Cys Val Lys Phe Thr Arg Gly Val Asp Phe Asn Trp
1               5                   10                  15

<210> SEQ ID NO 52
<211> LENGTH: 15
<212> TYPE: PRT
<213> ORGANISM: Homo sapiens

<400> SEQUENCE: 52

Cys Val Lys Phe Thr Arg Gly Val Asp Phe Asn Trp Gln Ala Gln
1               5                   10                  15

<210> SEQ ID NO 53
<211> LENGTH: 15
<212> TYPE: PRT
<213> ORGANISM: Homo sapiens

<400> SEQUENCE: 53

Phe Thr Arg Gly Val Asp Phe Asn Trp Gln Ala Gln Ala Leu Leu
1               5                   10                  15

<210> SEQ ID NO 54
<211> LENGTH: 15
<212> TYPE: PRT
<213> ORGANISM: Homo sapiens

<400> SEQUENCE: 54

Gly Val Asp Phe Asn Trp Gln Ala Gln Ala Leu Leu Ala Leu Gln
1               5                   10                  15

<210> SEQ ID NO 55
<211> LENGTH: 15
<212> TYPE: PRT
<213> ORGANISM: Homo sapiens

<400> SEQUENCE: 55

Phe Asn Trp Gln Ala Gln Ala Leu Leu Ala Leu Gln Glu Ala Ala
1               5                   10                  15

<210> SEQ ID NO 56
<211> LENGTH: 15
<212> TYPE: PRT
<213> ORGANISM: Homo sapiens

<400> SEQUENCE: 56

Gln Ala Gln Ala Leu Leu Ala Leu Gln Glu Ala Ala Glu Ala Phe
1               5                   10                  15

<210> SEQ ID NO 57
<211> LENGTH: 15
<212> TYPE: PRT
<213> ORGANISM: Homo sapiens

<400> SEQUENCE: 57

Ala Leu Leu Ala Leu Gln Glu Ala Ala Glu Ala Phe Leu Val His
1               5                   10                  15

<210> SEQ ID NO 58
<211> LENGTH: 15
<212> TYPE: PRT
<213> ORGANISM: Homo sapiens

<400> SEQUENCE: 58

Ala Leu Gln Glu Ala Ala Glu Ala Phe Leu Val His Leu Phe Glu
1               5                   10                  15

<210> SEQ ID NO 59

<211> LENGTH: 15
<212> TYPE: PRT
<213> ORGANISM: Homo sapiens

<400> SEQUENCE: 59

Glu Ala Glu Ala Phe Leu Val His Leu Phe Glu Asp Ala Tyr
1               5                   10                  15

<210> SEQ ID NO 60
<211> LENGTH: 15
<212> TYPE: PRT
<213> ORGANISM: Homo sapiens

<400> SEQUENCE: 60

Glu Ala Phe Leu Val His Leu Phe Glu Asp Ala Tyr Leu Leu Thr
1               5                   10                  15

<210> SEQ ID NO 61
<211> LENGTH: 15
<212> TYPE: PRT
<213> ORGANISM: Homo sapiens

<400> SEQUENCE: 61

Leu Val His Leu Phe Glu Asp Ala Tyr Leu Leu Thr Leu His Ala
1               5                   10                  15

<210> SEQ ID NO 62
<211> LENGTH: 15
<212> TYPE: PRT
<213> ORGANISM: Homo sapiens

<400> SEQUENCE: 62

Leu Phe Glu Asp Ala Tyr Leu Leu Thr Leu His Ala Gly Arg Val
1               5                   10                  15

<210> SEQ ID NO 63
<211> LENGTH: 15
<212> TYPE: PRT
<213> ORGANISM: Homo sapiens

<400> SEQUENCE: 63

Asp Ala Tyr Leu Leu Thr Leu His Ala Gly Arg Val Thr Leu Phe
1               5                   10                  15

<210> SEQ ID NO 64
<211> LENGTH: 15
<212> TYPE: PRT
<213> ORGANISM: Homo sapiens

<400> SEQUENCE: 64

Leu Leu Thr Leu His Ala Gly Arg Val Thr Leu Phe Pro Lys Asp
1               5                   10                  15

<210> SEQ ID NO 65
<211> LENGTH: 15
<212> TYPE: PRT
<213> ORGANISM: Homo sapiens

<400> SEQUENCE: 65

Leu His Ala Gly Arg Val Thr Leu Phe Pro Lys Asp Val Gln Leu
1               5                   10                  15

<210> SEQ ID NO 66
<211> LENGTH: 15
<212> TYPE: PRT

-continued

<213> ORGANISM: Homo sapiens

<400> SEQUENCE: 66

Gly Arg Val Thr Leu Phe Pro Lys Asp Val Gln Leu Ala Arg Arg
1               5                   10                  15

<210> SEQ ID NO 67
<211> LENGTH: 15
<212> TYPE: PRT
<213> ORGANISM: Homo sapiens

<400> SEQUENCE: 67

Thr Leu Phe Pro Lys Asp Val Gln Leu Ala Arg Arg Ile Arg Gly
1               5                   10                  15

<210> SEQ ID NO 68
<211> LENGTH: 15
<212> TYPE: PRT
<213> ORGANISM: Homo sapiens

<400> SEQUENCE: 68

Pro Lys Asp Val Gln Leu Ala Arg Arg Ile Arg Gly Leu Glu Glu
1               5                   10                  15

<210> SEQ ID NO 69
<211> LENGTH: 15
<212> TYPE: PRT
<213> ORGANISM: Homo sapiens

<400> SEQUENCE: 69

Val Gln Leu Ala Arg Arg Ile Arg Gly Leu Glu Glu Gly Leu Gly
1               5                   10                  15

<210> SEQ ID NO 70
<211> LENGTH: 15
<212> TYPE: PRT
<213> ORGANISM: Homo sapiens

<400> SEQUENCE: 70

Ala Arg Arg Ile Arg Gly Leu Glu Glu Gly Leu Gly Gly Ser Gly
1               5                   10                  15

<210> SEQ ID NO 71
<211> LENGTH: 15
<212> TYPE: PRT
<213> ORGANISM: Homo sapiens

<400> SEQUENCE: 71

Ile Arg Gly Leu Glu Glu Gly Leu Gly Gly Ser Gly Ser Gly Ser
1               5                   10                  15

<210> SEQ ID NO 72
<211> LENGTH: 15
<212> TYPE: PRT
<213> ORGANISM: Homo sapiens

<400> SEQUENCE: 72

Gly Gly Ser Gly Ser Gly Ser Gly Met His Arg Ala Val Asp Pro
1               5                   10                  15

<210> SEQ ID NO 73
<211> LENGTH: 15
<212> TYPE: PRT
<213> ORGANISM: Homo sapiens
<210> SEQ ID NO 74
<211> LENGTH: 15
<212> TYPE: PRT
<213> ORGANISM: Homo sapiens

<400> SEQUENCE: 73

Trp Ser Ser Cys Pro Pro His Pro Pro Arg Ser Ala Trp Leu
1               5                   10                  15

<210> SEQ ID NO 74
<211> LENGTH: 15
<212> TYPE: PRT
<213> ORGANISM: Homo sapiens

<400> SEQUENCE: 74

Ser His Gly Ser Ser Ser Gly His Pro Ser Lys Pro Tyr Tyr Ala
1               5                   10                  15

<210> SEQ ID NO 75
<211> LENGTH: 15
<212> TYPE: PRT
<213> ORGANISM: Homo sapiens

<400> SEQUENCE: 75

Gln Ala Leu Leu Arg Glu Pro Ala Gln Pro Gly Leu Trp Glu Gln
1               5                   10                  15

<210> SEQ ID NO 76
<211> LENGTH: 15
<212> TYPE: PRT
<213> ORGANISM: Homo sapiens

<400> SEQUENCE: 76

Ala Leu Arg Tyr Gly Gly Ser Phe Ala Glu Leu Gly Pro Arg Ile
1               5                   10                  15

<210> SEQ ID NO 77
<211> LENGTH: 15
<212> TYPE: PRT
<213> ORGANISM: Homo sapiens

<400> SEQUENCE: 77

Lys Val Leu Pro Pro Leu Glu Gln Val Trp Asn Leu Leu His Leu
1               5                   10                  15

<210> SEQ ID NO 78
<211> LENGTH: 15
<212> TYPE: PRT
<213> ORGANISM: Homo sapiens

<400> SEQUENCE: 78

Pro Pro Val Val Gln Pro Val Pro Pro Ala Ala Leu Ser Gly Pro
1               5                   10                  15

<210> SEQ ID NO 79
<211> LENGTH: 15
<212> TYPE: PRT
<213> ORGANISM: Homo sapiens

<400> SEQUENCE: 79

Thr Gly Leu Pro Pro Gly Leu Pro Leu Pro Pro Pro Leu Pro
1               5                   10                  15

<210> SEQ ID NO 80
<211> LENGTH: 15
<212> TYPE: PRT
<213> ORGANISM: Homo sapiens

<400> SEQUENCE: 80

Ser Pro Pro Phe Gln Leu Thr Lys Pro Gly Leu Trp Ser Thr Leu
1               5                   10                  15

<210> SEQ ID NO 81
<211> LENGTH: 15
<212> TYPE: PRT
<213> ORGANISM: Homo sapiens

<400> SEQUENCE: 81

Arg His Ser Leu Pro His Pro Tyr Pro Tyr Pro Ala Pro Ala Tyr
1               5                   10                  15

<210> SEQ ID NO 82
<211> LENGTH: 15
<212> TYPE: PRT
<213> ORGANISM: Homo sapiens

<400> SEQUENCE: 82

Pro Pro Gly Ala Glu Ser His Gly Cys Leu Pro Ala Thr Arg Pro
1               5                   10                  15

<210> SEQ ID NO 83
<211> LENGTH: 15
<212> TYPE: PRT
<213> ORGANISM: Homo sapiens

<400> SEQUENCE: 83

Pro Ala Ala Thr Thr Ala Cys Val Pro Tyr Ala Pro Ser Arg Pro
1               5                   10                  15

<210> SEQ ID NO 84
<211> LENGTH: 15
<212> TYPE: PRT
<213> ORGANISM: Homo sapiens

<400> SEQUENCE: 84

Arg Gly Val Glu Pro Asn Pro Gly Ile Pro Gly Ala Asp His Tyr
1               5                   10                  15

<210> SEQ ID NO 85
<211> LENGTH: 15
<212> TYPE: PRT
<213> ORGANISM: Homo sapiens

<400> SEQUENCE: 85

Arg Lys Pro Phe Leu Gly Ala Pro Ala Ala Thr Pro His Leu Ser
1               5                   10                  15

<210> SEQ ID NO 86
<211> LENGTH: 15
<212> TYPE: PRT
<213> ORGANISM: Homo sapiens

<400> SEQUENCE: 86

Pro Pro Pro Ala Trp Leu Lys Gly Pro Ala Cys Arg Ala Ala Arg
1               5                   10                  15

<210> SEQ ID NO 87
<211> LENGTH: 15
<212> TYPE: PRT
<213> ORGANISM: Homo sapiens

<400> SEQUENCE: 87

Pro Pro Pro Leu Pro His Arg Glu Gly Phe Leu Gly Pro Pro Ala
1               5                   10                  15

<210> SEQ ID NO 88
<211> LENGTH: 15
<212> TYPE: PRT
<213> ORGANISM: Homo sapiens

<400> SEQUENCE: 88

Thr Ser Ser Ser Met Ser Met Ser Gly Ser His Ser Ser Ser Pro
1               5                   10                  15

<210> SEQ ID NO 89
<211> LENGTH: 15
<212> TYPE: PRT
<213> ORGANISM: Homo sapiens

<400> SEQUENCE: 89

Arg Pro Pro Ser Pro Ala Gln Asn Pro Gln Asp Pro Pro Leu Val
1               5                   10                  15

<210> SEQ ID NO 90
<211> LENGTH: 15
<212> TYPE: PRT
<213> ORGANISM: Homo sapiens

<400> SEQUENCE: 90

Ser Phe Arg Arg Pro Glu Ser Pro Arg Pro Arg Val Ser Phe Pro
1               5                   10                  15

<210> SEQ ID NO 91
<211> LENGTH: 15
<212> TYPE: PRT
<213> ORGANISM: Homo sapiens

<400> SEQUENCE: 91

Val Pro Pro Gly Val Gly Glu Leu Pro Ala Arg Gly Pro Arg Leu
1               5                   10                  15

<210> SEQ ID NO 92
<211> LENGTH: 15
<212> TYPE: PRT
<213> ORGANISM: Homo sapiens

<400> SEQUENCE: 92

Leu Pro Asp Gly Leu Ala Asn Ile Met Lys Met Leu Asp Glu Ser
1               5                   10                  15

<210> SEQ ID NO 93
<211> LENGTH: 15
<212> TYPE: PRT
<213> ORGANISM: Homo sapiens

<400> SEQUENCE: 93

Lys Glu Pro Phe Ala Ser Leu Gln Ser Pro Phe Pro Thr Asp Thr
1               5                   10                  15

<210> SEQ ID NO 94
<211> LENGTH: 15
<212> TYPE: PRT
<213> ORGANISM: Homo sapiens

<400> SEQUENCE: 94

Thr Thr Ala Thr Gln Glu Glu Lys Lys Pro Pro Pro Pro Ala Leu
1               5                   10                  15

```
<210> SEQ ID NO 95
<211> LENGTH: 15
<212> TYPE: PRT
<213> ORGANISM: Homo sapiens

<400> SEQUENCE: 95

Pro Pro Pro Ser Pro Ala Ser Leu Leu Lys Ser Leu Ala Ser Val
1               5                   10                  15

<210> SEQ ID NO 96
<211> LENGTH: 15
<212> TYPE: PRT
<213> ORGANISM: Homo sapiens

<400> SEQUENCE: 96

Pro Leu Pro Thr Thr Gln Tyr Ser Pro Gly Pro Pro Ser Gly Ala
1               5                   10                  15

<210> SEQ ID NO 97
<211> LENGTH: 15
<212> TYPE: PRT
<213> ORGANISM: Homo sapiens

<400> SEQUENCE: 97

Ser Ser Ser Ser Gln Phe Ser Thr Ser Gly Gly Pro Trp Ala Arg
1               5                   10                  15

<210> SEQ ID NO 98
<211> LENGTH: 15
<212> TYPE: PRT
<213> ORGANISM: Homo sapiens

<400> SEQUENCE: 98

Pro Leu Ser Leu Pro Pro Ala Arg Ser Glu Ser Glu Val Leu Glu
1               5                   10                  15

<210> SEQ ID NO 99
<211> LENGTH: 15
<212> TYPE: PRT
<213> ORGANISM: Homo sapiens

<400> SEQUENCE: 99

Ala Asp Pro Val Asp Thr Ala Glu Pro Ala Asp Ser Gly Thr Glu
1               5                   10                  15

<210> SEQ ID NO 100
<211> LENGTH: 15
<212> TYPE: PRT
<213> ORGANISM: Homo sapiens

<400> SEQUENCE: 100

Ser Cys Lys Arg Arg Gln Lys Glu His Gln Lys Glu His Arg Arg
1               5                   10                  15

<210> SEQ ID NO 101
<211> LENGTH: 15
<212> TYPE: PRT
<213> ORGANISM: Homo sapiens

<400> SEQUENCE: 101

Lys Ala Lys Val Pro Lys Glu Lys Ser Arg Arg Val Leu Gly Asn
1               5                   10                  15

<210> SEQ ID NO 102
<211> LENGTH: 15
```

```
<212> TYPE: PRT
<213> ORGANISM: Homo sapiens

<400> SEQUENCE: 102

Ala Ser Lys Ala Lys Pro Pro Thr Ala Pro Ala Pro Pro Ser Ala
1               5                   10                  15

<210> SEQ ID NO 103
<211> LENGTH: 15
<212> TYPE: PRT
<213> ORGANISM: Homo sapiens

<400> SEQUENCE: 103

Glu Glu Ala Pro Glu Pro Pro Gly Val Ser Arg Ala Asp Met Leu
1               5                   10                  15

<210> SEQ ID NO 104
<211> LENGTH: 15
<212> TYPE: PRT
<213> ORGANISM: Homo sapiens

<400> SEQUENCE: 104

Glu Ser Gly Asp Lys Glu Thr Phe Ile Ala Ser Glu Val Glu Glu
1               5                   10                  15

<210> SEQ ID NO 105
<211> LENGTH: 15
<212> TYPE: PRT
<213> ORGANISM: Homo sapiens

<400> SEQUENCE: 105

Ser Arg Asn Ala Lys Val Lys Gly Lys Phe Arg Glu Ser Tyr Leu
1               5                   10                  15

<210> SEQ ID NO 106
<211> LENGTH: 15
<212> TYPE: PRT
<213> ORGANISM: Homo sapiens

<400> SEQUENCE: 106

Leu Asn Pro Pro Thr Pro Ser Ile Tyr Leu Glu Ser Lys Arg Asp
1               5                   10                  15

<210> SEQ ID NO 107
<211> LENGTH: 15
<212> TYPE: PRT
<213> ORGANISM: Homo sapiens

<400> SEQUENCE: 107

Arg Gly Leu Ala Gly Ser Leu Arg Leu Asn Leu Gly Leu Phe Ser
1               5                   10                  15

<210> SEQ ID NO 108
<211> LENGTH: 15
<212> TYPE: PRT
<213> ORGANISM: Homo sapiens

<400> SEQUENCE: 108

Gln Pro Ser Asp Glu Asn Trp Asp Leu Thr Gly Thr Arg Gln Ile
1               5                   10                  15

<210> SEQ ID NO 109
<211> LENGTH: 15
<212> TYPE: PRT
<213> ORGANISM: Homo sapiens
```

-continued

<400> SEQUENCE: 109

Ser Ser Phe Gln Glu Ser Leu Gln Glu Glu Lys Glu Ser Glu Asp
1               5                   10                  15

<210> SEQ ID NO 110
<211> LENGTH: 15
<212> TYPE: PRT
<213> ORGANISM: Homo sapiens

<400> SEQUENCE: 110

Lys Asn His His Ile Ile Lys Phe Gly Thr Asn Ile Asp Leu Ser
1               5                   10                  15

<210> SEQ ID NO 111
<211> LENGTH: 15
<212> TYPE: PRT
<213> ORGANISM: Homo sapiens

<400> SEQUENCE: 111

Val Thr Ser Thr Gly Asn Met Leu Ser His Val Gly His Thr Ile
1               5                   10                  15

<210> SEQ ID NO 112
<211> LENGTH: 15
<212> TYPE: PRT
<213> ORGANISM: Homo sapiens

<400> SEQUENCE: 112

Gln Glu Asn Asn Asn Phe Cys Ser Val Asn Ile Asn Ile Gly Pro
1               5                   10                  15

<210> SEQ ID NO 113
<211> LENGTH: 15
<212> TYPE: PRT
<213> ORGANISM: Homo sapiens

<400> SEQUENCE: 113

Asp Arg His Gly Val Asp Tyr Leu Thr Gly Ser Trp Trp Pro Ile
1               5                   10                  15

<210> SEQ ID NO 114
<211> LENGTH: 15
<212> TYPE: PRT
<213> ORGANISM: Homo sapiens

<400> SEQUENCE: 114

Leu Val Trp Ile Asn Ala Gly Thr Val His Trp Val Gln Ala Thr
1               5                   10                  15

<210> SEQ ID NO 115
<211> LENGTH: 15
<212> TYPE: PRT
<213> ORGANISM: Homo sapiens

<400> SEQUENCE: 115

Ala Leu Glu Arg Tyr Glu Trp Asn Glu Val Lys Asn Val Lys Ser
1               5                   10                  15

<210> SEQ ID NO 116
<211> LENGTH: 15
<212> TYPE: PRT
<213> ORGANISM: Homo sapiens

<400> SEQUENCE: 116

```
Asp Leu Phe Lys Met Ile Lys Phe Cys Leu Leu Gln Ser Met Lys
1               5                   10                  15

<210> SEQ ID NO 117
<211> LENGTH: 15
<212> TYPE: PRT
<213> ORGANISM: Homo sapiens

<400> SEQUENCE: 117

Arg Val Lys Asp Glu Pro Ala Tyr Tyr Cys Asn Glu Cys Asp Val
1               5                   10                  15

<210> SEQ ID NO 118
<211> LENGTH: 15
<212> TYPE: PRT
<213> ORGANISM: Homo sapiens

<400> SEQUENCE: 118

His Cys Glu Gly Cys Ala Arg Arg Arg Ser Ala Gly Leu Gln Gly
1               5                   10                  15

<210> SEQ ID NO 119
<211> LENGTH: 15
<212> TYPE: PRT
<213> ORGANISM: Homo sapiens

<400> SEQUENCE: 119

Leu Val Arg Ala Arg Arg Ala Arg Gly Gln Arg Arg Arg Ala Leu
1               5                   10                  15

<210> SEQ ID NO 120
<211> LENGTH: 15
<212> TYPE: PRT
<213> ORGANISM: Homo sapiens

<400> SEQUENCE: 120

Ala Phe Ser Pro Gln Ala Pro Ala Ser Thr Ser Arg Gly Ser Gly
1               5                   10                  15
```

MARKER SEQUENCES FOR DIAGNOSING AND STRATIFYING SYSTEMIC SCLEROSIS PATIENTS

RELATED APPLICATIONS

This application is a national stage application (under 35 U.S.C. § 371) of PCT/EP2015/065268, filed Jul. 4, 2015, which claims benefit of European Application No. 14176035.5, filed Jul. 7, 2014.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074027_0036. The size of the text file is 41 KB, and the text file was created on Jan. 6, 2017.

The present invention relates to methods for identifying markers for systemic sclerosis (SSc; also scleroderma or Progressive Systemic Sclerosis (PSS)) and to the markers identified with the aid of this method, which can differentiate between SSc and other autoimmune diseases on the one hand and between different SSc subgroups on the other hand. The invention also relates to panels, diagnostic devices and test kits which comprise these markers, and to the use and application thereof, for example for the diagnosis, prognosis and therapy control of SSc. The invention also relates to methods for screening and for validating active substances for use in SSc subgroups.

SSc is a chronic, inflammatory, rheumatic disease, which counts among the classic immunological connective tissue diseases (collagenoses).

SSc is a heterogeneous disease with excessive fibrosis of the skin. Further organ systems, such as the lungs, gastrointestinal area, kidneys, heart and blood vessels can also be affected. In addition, joint symptoms (arthritis) also occur.

SSc is a very rare disease. The incidence is approximately 0.5-1.5/100,000 individuals/year. It mostly occurs between the ages of 30 and 50. Women are 10-15 times more likely to be affected than men (LeRoy et al. 1988).

Clinically, a distinction can be made between limited and diffuse SSc in accordance with LeRoy et al. (1998). In early phases of the disease, it is often difficult to classify patients unambiguously, with this being referred to as undifferentiated SSc. If, in addition to scleroderma, fundamental symptoms of other rheumatic diseases also occur, reference is made to scleroderma overlap syndrome or overlap syndrome.

The limited form of SSc occurs at a frequency of up to 60%. This is characterised by fibrosis of the hands and feet, which spreads to below the elbows and knee joints. Raynaud's phenomenon often exists already for many years prior to the appearance of skin fibrosis. Gastrointestinal changes (difficulty in swallowing) and pulmonary arterial hypertension (PAH) also often occur. The limited form also includes CREST syndrome: calcinosis cutis, Raynaud's phenomenon, esophageal dysmotility, sclerodactyly, and telangiectasia.

The diffuse form is the quicker and more severe form of SSc. In this case the fibrosis spreads past the elbows over the body and face. In contrast to the limited form, skin fibroses occur already 1-2 years after the appearance of Raynaud's phenomenon.

In the case of scleroderma overlap syndrome, symptoms of further non-organ-specific autoimmune diseases, such as myositis, lupus erythematosus/SLE, Sjögren's syndrome, and rheumatoid arthritis/RA, also occur in addition to the skin symptoms of scleroderma.

Patients with undifferentiated SSc have Raynaud's syndrome and have the swollen fingers typical of SSc and pulmonary arterial hypertension. Only some of the patients later actually develop diffuse or limited SSc.

The diagnosis of SSc can be provided on the basis of the clinical picture with the typical skin changes. This can be difficult, however, in the early stages of the disease. In addition, the detection of antinuclear antibodies (ANAs) is used. ANAs can be detected in approximately 90% of SSc patients. However, the ANA test is not specific for SSc, since other collagenoses and up to 20% of healthy individuals will test positively. The three most important autoantibodies in the case of SSc are anti-topoisomerase I (Scl-70), anti-centromere (CENP), and anti-RNA polymerase III (anti-RNAP III). These autoantibodies have a high specificity for SSc and are often associated with a subform of SSc. However, these 3 autoantibodies are suitable only to a limited extent for subtyping of SSc, since they do not occur exclusively in one subtype and their frequency can deviate distinctly in different ethnicities. Anti-topoisomerase antibodies have a high specificity for SSc and are detectable in approximately 30% of patients having diffuse SSc. Anti-centromere antibodies are, by contrast, detectable in approximately 50-60% of patients having limited SSc and in 10% of patients having diffuse SSc. The two autoantibodies are mutually exclusive and are detectable jointly in patients only in very rare cases. Anti-RNAP III antibodies are detectable more frequently in the diffuse form and constitute a risk factor for renal crisis. On the whole, only approximately 70% of SSc patients can be identified diagnostically using the autoantibodies against anti-topoisomerase, anti-centromere and anti-RNAP (Mierau et al. 2011; Mehra et al. 2013).

Antibodies against U1-RNP and PM-Scl antibodies also occur more rarely. These, however, have only a low specificity for SSc: anti-PM-Scl antibodies are often detected in patients having polymyositis/SSc overlap syndrome. Antibodies against U1-RNP are detectable both in the case of SSc and in the case of mixed connective tissue diseases (MCTD) and SLE. In approximately one third of patients, antibodies against typical collagenosis antigens, such as Rho52/SS-A, Ro60/SS-B, and citrullinated peptides (ACPA) and rheumatoid factors are also detected.

In clinical practice, the diagnosis of an early form of SSc and classification thereof into the subgroups constituted by diffuse, limited or overlap syndrome is often difficult, since not all symptoms are yet present or approximately 10-30% of patients carry symptoms of a different collagenosis (connective tissue disease). Since the various subforms have a very different prognosis, there is a substantial need for biomarkers for improved diagnosis of SSc and for a classification into SSc subgroups. There is also a great need for prognostic and predictive biomarkers.

A further problem of the currently used diagnostic methods is that the suitability of the previously tested autoantigens for the diagnosis of organ involvement and complications is disputed, and partly conflicting data has been published. Furthermore it is desirable with respect to the application in individualized medicine to have markers available that are easy to produce and handle, opening up a broad field of diagnostic applications.

This object is achieved in accordance with the invention by markers that detect certain characteristic regions of autoantigens related to SSc. These characteristic regions are one or more short sequences, which optionally may be modified and, either alone or collectively, form a pattern characteristic of SSc and/or one or more SSc subgroups. These short makers are easy to produce and handle and open up a broad field of practical diagnostic applications within the scope of individualized medicine.

The term systemic sclerosis (SSc) is defined for example in Pschyrembel, Clinical Dictionary (2012 edition, DE GRUYTER).

The invention thus relates to a marker for detecting systemic sclerosis (SSc), characterised in that the marker comprises one or more peptide sequences having a respective length of no more than 35 amino acids.

In a preferred embodiment, the marker according to the invention is characterised in that the one or more peptide sequences have a respective length of no more than 25 amino acids.

In a further preferred embodiment, the marker according to the invention is characterised in that the one or more peptide sequences have a respective length of no more than 15 amino acids, and preferably of no more than 12 or 13 amino acids.

In a further embodiment of the invention, the marker is a binding region.

In a further embodiment of the invention, the marker is an epitope. The epitope can, for example, be a linear or a conformational epitope.

In a further preferred embodiment, the marker according to the invention is characterised in that the peptide sequence is selected from, or the peptide sequences are selected independently of one another from,

```
                                    SEQ ID No. 1
SPQPSASSSSQFSTSGGPWARERRAGEEPV

SEQ ID No. 2
LPAPLPPSHGSS

SEQ ID No. 3
SPQPSASSSSQF

SEQ ID No. 4
SSQFSTSGGPWAR

SEQ ID No. 5
REKLNPPTPSIYL

SEQ ID No. 6
GGPWARERRAGEEPV

SEQ ID No. 7
PREKLNPPTPSIYL

SEQ ID No. 8
YQYQLALERYEWNEV

SEQ ID No. 9
PRRRSRKPEAPRRRSPSPTPTPGPSRRGPSLGAS

SEQ ID No. 10
SPSPTPTPGPSR

SEQ ID No. 11
GPSRRGPSLGAS

SEQ ID No. 12
TPTPGPSRRGPS

SEQ ID No. 13
RSPSPTPTPGPSR

SEQ ID No. 14
PRRRSRKPEAPR

SEQ ID No. 15
RSPSPTPTPGPSR

SEQ ID No. 16
APRRRSPSPTPTPGP

SEQ ID No. 17
RRRSPSPTPTPGPSR

SEQ ID No. 18
SPSPTPTPGPSRRGP,
``` homologues of sequences SEQ ID No. 1 to 18 with at least 95% homology, subsequences of SEQ ID No. 1 to 18 and subsequences of homologues of SEQ ID No. 1 to 18 with at least 95% homology.

In a preferred embodiment, the marker comprises SEQ ID No. 2.

In a preferred embodiment, the marker comprises SEQ ID No. 3.

In a preferred embodiment, the marker comprises SEQ ID No. 4.

In a preferred embodiment, the marker comprises SEQ ID No. 5.

In a preferred embodiment, the marker comprises SEQ ID No. 2 and SEQ ID No. 3.

In a preferred embodiment, the marker comprises a subsequence of SEQ ID No. 1. The subsequence preferably has a length of 12 or 13 amino acids.

In a preferred embodiment, the marker comprises at least two subsequences of SEQ ID No. 1. The subsequences preferably have a length of 12 or 13 amino acids.

In a preferred embodiment, the marker comprises SEQ ID No. 10.

In a preferred embodiment, the marker comprises SEQ ID No. 11.

In a preferred embodiment, the marker comprises SEQ ID No. 12.

In a preferred embodiment, the marker comprises SEQ ID No. 13.

In a preferred embodiment, the marker comprises SEQ ID No. 14.

In a preferred embodiment, the marker comprises SEQ ID No. 10 and SEQ ID No. 11.

In a preferred embodiment, the marker comprises a subsequence of SEQ ID No. 9. The subsequence preferably has a length of 12 or 13 amino acids.

In a preferred embodiment, the marker comprises at least two subsequences of SEQ ID No. 9. The subsequences preferably have a length of 12 or 13 amino acids.

In a further embodiment of the invention, the marker is characterised in that the marker comprises one or more sequences that code for one or more of the peptide sequences SEQ ID No. 1-18, one or more homologues of sequences SEQ ID No. 1 to 18 with at least 95% homology, one or more subsequences of SEQ ID No. 1 to 18, one or more subsequences of the homologues of SEQ ID No. 1 to 18 with at least 95% homology.

The invention also relates to the use of at least one marker according to the invention. The invention relates to the use of at least one marker according to the invention for diagnosis, for example for early diagnosis or for differential diagnosis, in particular for distinguishing SSc from other autoimmune diseases or from rheumatic diseases. The invention relates to the use of at least one marker according to the invention for prognosis. The invention relates to the use of at least one marker according to the invention for therapy control, for example for active substance selection and/or for selecting the dosage. The invention relates to the use of at least one marker according to the invention for therapy monitoring. The invention relates to the use of at least one marker according to the invention for stratification. The invention relates to the use of at least one marker according to the invention for aftercare in the case of SSc.

The invention relates to the use of at least one marker according to the invention for identifying SSc subgroups. The invention relates to the use of at least one marker according to the invention for the diagnosis of SSc subgroups, for example for the early diagnosis or for the differential diagnosis of SSc subgroups, in particular for distinguishing individual SSc subgroups from other SSc subgroups and/or from other autoimmune diseases or rheumatic diseases. The invention relates to the use of at least one marker according to the invention for the prognosis of individual SSc subgroups. The invention relates to the use of at least one marker according to the invention for therapy control in individual SSc subgroups, for example for active substance selection and/or for selecting the suitable dosage for individual SSc subgroups. The invention relates to the use of at least one marker according to the invention for the therapy monitoring of individual SSc subgroups. The invention relates to the use of at least one marker according to the invention for the stratification of individual SSc subgroups. The invention relates to the use of at least one marker according to the invention for the aftercare of individual SSc subgroups. SSc subgroups are, for example, diffuse SSc (dSSc), limited SSc (lSSc) or SSc overlap syndrome (SSc-OS). For example, the marker SEQ ID No. 3 is suitable for this use. For example, the marker SEQ ID No. 4 is suitable for this use. For example, the marker SEQ ID No. 5 is suitable for this use. For example, the marker SEQ ID No. 12 is suitable for this use. For example, the marker SEQ ID No. 13 is suitable for this use. For example, the marker SEQ ID No. 14 is suitable for this use. Combinations of the aforementioned sequences are also suited.

The invention also relates to a panel (arrangement) of markers for use with SSc, comprising at least one marker according to the invention. The invention also relates to a panel of markers for use with SSc, comprising at least two markers according to the invention. The invention also relates to a panel of markers for use with SSc, comprising at least three or four markers according to the invention. Corresponding panels can include further markers or components. The invention relates to a panel of markers for SSc or SSc subgroups, comprising at least two different markers selected independently of one another from the sequences SEQ ID No. 1 to 18, homologues of sequences SEQ ID No. 1 to 18 with at least 95% homology, and subsequences of SEQ ID No. 1 to 18 and subsequences of homologues of SEQ ID No. 1 to 18 with at least 95% homology.

The invention relates to a panel of markers for use with SSc comprising SEQ ID No. 2 and SEQ ID No. 3. The invention relates to a panel of markers for use with SSc comprising SEQ ID No. 10 and SEQ ID No. 11. The invention relates to a panel of markers for use with SSc comprising SEQ ID No. 2, SEQ ID No. 3 and SEQ ID No. 10. The invention relates to a panel of markers for use with SSc comprising SEQ ID No. 2, SEQ ID No. 3 and SEQ ID No. 11. The invention relates to a panel of markers for use with SSc comprising SEQ ID No. 2, SEQ ID No. 10 and SEQ ID No. 11. The invention relates to a panel of markers for use with SSc comprising SEQ ID No. 3, SEQ ID No. 10 and SEQ ID No. 11. The invention relates to a panel of markers for use with SSc comprising SEQ ID No. 2, SEQ ID No. 3, SEQ ID No. 10 and SEQ ID No. 11. A person skilled in the art will be able to compile further panels by appropriately combining the markers according to the invention in analogous fashion.

On account of the high clinical and serological heterogeneity of the SSc disease, it is difficult to diagnose SSc unambiguously using just one biomarker. It is therefore often necessary to combine (where possible) uncorrelated autoantigens to form what are known as panels of markers (biomarker panels for SSc). For example, within the scope of individualised medicine, corresponding panels of markers for SSc can be composed individually for the relevant SSc subtype (subgroup) for individual patients or patient groups. A corresponding panel can be embodied for example in the form of an arrangement, an array, or also one or more beads. The invention thus relates to an arrangement comprising one or more markers according to the invention, a protein array comprising one or more markers according to the invention, and a bead (pellet or platelet) comprising one or more markers according to the invention.

The invention also relates to a diagnostic device for use with SSc, comprising at least one marker according to the invention or at least one panel according to the invention. The invention also relates to a test kit for use with SSc, comprising at least one marker according to the invention or at least one panel according to the invention.

The invention also relates to a method for the diagnosis, for example for the early diagnosis and/or for the differential diagnosis of SSC. The invention also relates to a method for the prognosis of SSc. The invention also relates to a method for therapy control, for example for active substance selection and/or for selecting the dosage in the case of SSc. The invention also relates to a method for the therapy monitoring of SSc. The invention also relates to a method for the aftercare of SSc. Corresponding methods can comprise the following steps:
 a. Bringing at least one marker according to the invention, for example a binding region or an epitope or a panel according to the invention or an antibody according to the invention
 b. into contact with bodily fluid or a tissue sample from an individual to be tested, and
 c. detecting an interaction of the bodily fluid or of the tissue sample with the one or more markers or the panel or the antibody from a.

The invention also relates to a composition comprising at least one marker according to the invention, for example a binding region or an epitope. The invention also relates to a pharmaceutical composition for specific application in the case of SSc, which comprises at least one marker according to the invention. The invention also relates to a drug for specific application in the case of SSc, which comprises at least one marker according to the invention. Corresponding (pharmaceutical) compositions and drugs can comprise further additives and/or auxiliary agents.

The invention also relates to an antibody for specific application for the treatment of SSc. The invention relates to an antibody for specific application for the treatment of SSc, comprising at least one binding region according to the invention or an epitope according to the invention. The invention relates to an antibody for specific application for the treatment of SSc, comprising at least one epitope according to the invention. The invention relates to an antibody for specific application for the treatment of SSc, comprising at least one peptide sequence SEQ ID No. 1 to 18. The invention relates to an antibody for specific application for the treatment of SSc, comprising at least one homologue of the peptide sequence SEQ ID No. 1 to 18 with at least 95% homology. The invention relates to an antibody for specific application for the treatment of SSc, comprising at least one subsequence SEQ ID No. 3 to 18. The invention relates to an antibody for specific application for the treatment of SSc, comprising at least one subsequence of the homologues of SEQ ID No. 1 to 18 with at least 95% homology.

The invention also relates to a target for the therapy of SSc selected from the markers according to the invention, for example a binding region or an epitope, for example selected from sequences SEQ ID No. 1 to 18, the homologues of sequences SEQ ID No. 1 to 18 with at least 95% homology, the subsequences of SEQ ID No. 1 to 18 and the subsequences of the homologues of SEQ ID No. 1 to 18 with at least 95% homology, and the nucleic acids coding for sequences SEQ ID No. 1 to 18, the homologues thereof, subsequences and homologues of the subsequences.

In a further embodiment, the invention relates to a drug or an active substance or a prodrug developed for SSc and obtainable through the use of an SSc marker according to the invention.

One embodiment of the composition is an affinity material comprising one or more markers according to the invention. The affinity material can be used, for example, for carrying out an apharesis or blood washing for patients with SSc. The invention thus relates to the use of the markers according to the invention, preferably in the form of an arrangement, as affinity material for carrying out a blood washing in the broader sense, wherein substances from bodily fluids from a patient with SSc, such as blood or plasma, bind to the markers according to the invention and consequently can be removed selectively from the bodily fluid.

The invention also relates to a method for screening active substances for use with SSc, in which
 a. at least one marker according to the invention, for example a binding region or an epitope or a panel according to the invention or an antibody according to the invention
 b. is brought into contact with a substance to be analyzed, and
 c. an interaction of the substance to be analyzed with the one or more markers, the panel or the antibodies from a. is detected.

The invention relates to the use of one or more markers according to the invention together with already known and/or new active substances (companion diagnostics). The invention relates to the use of one or more markers according to the invention for defining patient groups, for example to recruit dSSc, lSSc or SSc-OS subgroups for drug studies. The invention relates to the use of one or more markers according to the invention for identifying specific antibody signatures in SSc patient subgroups. The invention relates to the use of one or more markers according to the invention for the individually tailored diagnosis and/or therapy of individual patients, patient groups, cohorts, population groups, variants of SSc, and stages of SSc. The invention relates to the use of one or more markers according to the invention for the analysis of autoantibody profiles of patients, in particular for the qualitative and/or quantitative analysis of autoantibodies and/or for monitoring changes of autoantibody profiles associated with SSc or SSc subgroups, for example in bodily fluids such as serum, tissue or tissue samples of the patient. The invention essentially relates to the use of one or more markers according to the invention, in which the detection of an interaction of the bodily fluid or of the tissue sample and the one or more markers according to the invention is carried out, thereby mapping an SSc- or SSc-subgroup-associated autoantibody profile of the patient or of a cohort or of a population group. The invention relates to the use of one or more markers according to the invention, in which the detection of an interaction of the bodily fluid or of the tissue sample with the one or more markers according to the invention allows the prediction of a course of the disease (prognosis). The invention relates to the use of one or more markers according to the invention, in which the detection of an interaction of the bodily fluid or of the tissue sample with the one or more markers according to the invention enables a prediction with respect to a response or non-response to a therapy or an active substance (such as therapy control, active substance selection). The invention relates to the use of one or more markers according to the invention for the analysis of autoantibody profiles of patients, in particular for the quantitative analysis and/or for the monitoring of changes of autoantibody profiles of SSc patients. An interaction of the bodily fluid or of the tissue sample with the one or more SSc markers can be detected, for example, by a probe, in particular by an antibody.

In a preferred embodiment at least 2, for example 3, 4, 5, 6, 7, 8, 9, 10 or more markers according to the invention are used together or in combination, either simultaneously or in succession.

The invention comprises the markers according to the invention on a solid substrate, for example a filter, a membrane, a small platelet or ball, for example a magnetic or fluorophore-labelled ball, a silicon wafer, a bead, a chip, a mass spectrometry target, or a matrix, or the like. Different materials are suitable as substrates and are known to a person skilled in the art, for example glass, metal, plastic, filter, PVDF, nitrocellulose, or nylon (for example Immobilon P Millipore, Protran Whatman, Hybond N+ Amersham).

The substrate for example can correspond to a grid with the dimensions of a microtitre plate (8-12 well strips, 96 wells, 384 wells or more), of a silicon wafer, of a chip, of a mass spectrometry target, or of a matrix. In one embodiment of the panel, the particular SSc marker can be represented in different quantities in one or more regions of the panel. This allows a variation of the sensitivity. The regions may each have a totality of SSc markers, that is to say a sufficient number of different SSc markers, in particular 2, 3, 4, 5, 6, 7, 8, 9 or 10 or more, 20 to 50 (numerically) or more, preferably more than 100, particularly preferably 150 or more, for example 25,000 or 5,000 or 10,000. It is possible to use identical markers and/or different markers.

A "protein array" in the sense of this invention is the systematic arrangement of SSc markers on a solid substrate, wherein the substrate can have any shape and/or size, and wherein the substrate is preferably a solid substrate.

The SSc markers of the arrangement are fixed on the substrate, preferably spotted or immobilised, printed on or the like, in particular in a reproducible manner. One or more SSc markers can be present multiple times in the totality of all SSc markers and may be present in different quantities based on a spot. Furthermore, the SSc markers can be standardised on the substrate (for example by means of serial dilution series of, for example, human globulins as internal calibrators for data normalisation and quantitative evaluation). A standard (for example a gold standard) can also be applied to the substrate where necessary. In a further embodiment, the one or more SSc markers are present in the form of clone sequences or clones.

In the uses or applications described in the present application, the markers according to the invention can be combined, supplemented or extended with known biomarkers for SSc or biomarkers for other diseases. With a combination of this type, a proportion of markers according to the invention of preferably at least 50%, preferably 60%, and particularly preferably 70% or more is comprised.

In a preferred embodiment, the use of the SSc markers is implemented outside the human or animal body, for example the diagnosis is performed ex vivo/in vitro.

In the sense of this invention, the term "diagnosis" means the positive determination of SSc with the aid of the markers according to the invention and the assignment of the patients or symptoms thereof to the disease SSc. The term 'diagnosis' comprises medical diagnostics and examinations in this regard, in particular in vitro diagnostics and laboratory diagnostics, as well as proteomics and nucleic acid blotting. Additional examinations may be required for validation and to exclude other illnesses. The term 'diagnosis' therefore includes in particular the differential diagnosis of SSc by means of the markers according to the invention.

In the sense of this invention, "stratifying (also: stratification) or therapy control" means that, for example, the methods according to the invention allow decisions for the treatment and therapy of the patient, whether it is the hospitalisation of the patient, the use, efficacy and/or dosage of one or more drugs, a therapeutic measure or the monitoring of the course of a disease and the course of therapy or aetiology or classification of a disease, for example into a new or existing sub-type, or the differentiation of diseases and patients thereof. In a further embodiment of the invention, the term "stratification" in particular includes the risk stratification with the prognosis of an "outcome" of a negative health event. The stratification of patients with SSc into new or established SSc subgroups as well as the expedient selection of patient groups for the clinical development of new therapeutic agents is also included. The term 'therapy control' also includes dividing the patients into responders and non-responders with respect to a therapy or the treatment course thereof.

In accordance with the invention, "therapy control" means, for example, the prediction and monitoring of the response to a drug or to a therapy as well as aftercare.

"Prognosis" means the prediction of the course of a disease.

Within the scope of this invention, the term "patient" is understood to mean any test subject, any individual (human or mammal), with the provision that the test subject or individual is tested for SSc.

Markers according to the invention are nucleic acid sequences and/or amino acid sequences, preferably amino acid sequences according to the definition in the appended sequence listing (SEQ ID No. 1 to SEQ ID No. 18), homologues and subsequences thereof, wherein modified nucleic acid and amino acid sequences are also included. The marker according to the invention can result in an interaction with SSc-specific substances from the bodily fluid or tissue sample from a patient with SSc (for example antigen (epitope)/antibody (paratope) interaction). The SSc-specific substances from the bodily fluid or tissue sample occur either only in an amplified manner or at least in an amplified manner in the case of SSc or are expressed, whereas these substances are not present in patients without SSc or healthy individuals, or at least are present to a lesser extent (smaller amount, lower concentration). The markers according to the invention for SSc are additionally characterised in that they interact with substances from the bodily fluid or tissue sample from patients with SSc, because certain substances no longer occur or are no longer expressed or occur or are expressed at least in a much lower amount/concentration in the case of SSc, whereas these substances are present or are at least present to a much higher extent in patients without SSc. Markers for SSc can also be present in healthy test subjects, however the amount (concentration) thereof changes, for example, with the development, establishment and therapy of SSc. One or more markers can in this way map a profile of substances from bodily fluid and tissue sample, for example an SSc-associated autoantibody profile of the patient in question. Markers according to the invention are biomarkers for SSc.

In a particularly preferred embodiment, the marker according to the invention identifies and/or binds to autoantibodies which are present (intensified) or are present to a lower extent (or no longer) during the course of the development, establishment and therapy of SSc. Within the scope of the present invention, the autoantibodies which are formed with the occurrence and during the course of the development of SSc and/or of which the expression is up-regulated or down-regulated are detected in particular. These autoantibodies can be detected with the aid of the methods and markers according to the invention, and the detection and monitoring (for example of the amount) thereof can be used for the early identification, diagnosis and/or therapy monitoring/therapy control and the prognosis and prediction of the risk of the re-occurrence of SSc within the scope of the aftercare.

The autoantibody profiles can be sufficiently characterised with the use of just a single SSc marker. In other cases, two or more SSc markers are necessary in order to map an autoantibody profile which is specific for SSc. The number of markers used can differ, for example, within the scope of the use in diagnostic devices. While rapid or routine tests, which the patient carries out at home, comprise only one, 2, 3 or 4 (few) markers, a highly sensitive diagnostic test can comprise several to many, such as 5-20 or more, markers.

In one embodiment of the invention, autoantibodies can be detected using SSc markers; for example, these are homologues of the sequences SEQ ID No. 18. In another embodiment of the invention, these autoantibodies can be detected using SSc markers which derive from the same individual. Autoantibodies can be formed by the patient already many years prior to the occurrence of the first symptoms of disease. An early identification, diagnosis and also prognosis and preventative treatment or lifestyle change and other possibilities for prevention would therefore be possible years prior to the visible outbreak of the disease. The devices, means and methods according to the invention thus enable a very early intervention compared with known methods, which significantly improves the prevention, treatment possibilities and effects of SSc.

Since the SSc-associated autoantibody profiles change during the establishment and treatment/therapy of SSc, the invention also enables the detection and monitoring of SSc at any stage of the development and treatment and also monitoring within the scope of SSc aftercare. The means according to the invention, for example a corresponding diagnostic device or a test kit, also allow simple handling at home by the patient and an economical routine precautionary measure for early identification.

Compared with other biomarkers, the detection of SSc-associated autoantibodies for example in the serum or plasma of patients has the advantage of high stability and storage capability and good detectability. The presence of autoantibodies also is not subject to a circadian rhythm, and therefore the sampling is independent of the time of day, food intake, and the like.

The invention relates to the use of one or more markers according to the invention for the detection in a bodily fluid, in particular blood, whole blood, blood plasma, blood serum, patient serum, urine, cerebrospinal fluid, synovial fluid or a tissue sample from the patient. The invention relates in particular to the use of the markers according to the invention on these bodily fluids and tissue samples for early detection, diagnosis, prognosis, therapy control and aftercare. However, this list is not exhaustive and it is also possible, for example, to couple these with DNA tests.

Homologues of the markers SEQ ID No. 1 to 18 according to the invention are included. Within the sense of the invention, homologues are those with homology of the amino or nucleic acid sequence (sequence homologues) and those in which the corresponding sequence is modified, for example the protein variants, which have the same amino acid sequence, but differ with regard to the modification, in particular the post-translational modification. In accordance with the invention, modifications of the nucleic acid sequence and of the amino acid sequence, for example citrullination, acetylation, phosphorylation, glycosylation, methylation, or polyA strand extensions and further modifications known as appropriate to a person skilled in the art are included.

Sequence homologues of the markers and the subsequences thereof are nucleic acid sequences and/or protein sequences. Sequence homologues of the markers SEQ ID No. 1-18 are protein sequences that have an identity of at least 90%, preferably 95%, particularly preferably 96% or 97% or more, for example 98% or 99%. Sequences that, in addition to sequences SEQ ID No. 1 to 18, also comprise further sequences are also included in accordance with the invention, wherein these further sequences, however, are not identical to those of the native protein in question from which the markers according to the invention derive. In accordance with the invention, proteins and peptides that comprise one or more of the markers according to the invention, but are not identical to the native proteins in question from which the markers according to the invention are derived, are also included. In accordance with the invention, nucleic acids that code for the protein sequence of the homologues are also included.

The invention also relates to subsequences of the markers according to the invention with the sequence SEQ ID No. 1 to 18 and the homologues thereof. Subsequences are those amino acid sequences that are shortened compared with the entire sequence SEQ ID No. 1 to 18. Here, the deletion may occur at the end or the ends and/or within the peptide sequence. For example, subsequences that have one amino acid less than the sequences SEQ ID No. 1 to 18 are comprised. Subsequences that have 2 fewer amino acids than the sequences SEQ ID No. 1 to 18 are also comprised. For example, subsequences that have 3 fewer amino acids than the sequences SEQ ID No. 1 to 18 are also comprised. Subsequences that have 4 or 5 fewer amino acid than the sequences SEQ ID No. 1 to 18 are also comprised. In accordance with the invention also included are markers according to the invention that differ from sequences SEQ ID No. 1 to 18 in that they contain one or more insertions, wherein the insertions for example are 1 to 10 or more amino acids long, for example 1 to 10 or more amino acids, for example 1, 2, 3, 4 to 5 amino acids long, and the sequences are otherwise identical or homologous to sequences SEQ ID No. 1 to 18. Subsequences that have at least 95%, preferably at least 97%, particularly preferably at least 98% or 99%, of the length of the markers according to the invention with sequences SEQ ID No. 1 to 18 are particularly preferred.

In addition, the SSc markers can be present in the respective form in the form of a fusion protein, which for example contains at least one affinity epitope or "tag", wherein the tag is selected for example from c-myc, His tag, Arg tag, FLAG, alkaline phosphatase, V5 tag, T7 tag or Strep tag, HAT tag, NusA, S tag, SBP tag, thioredoxin, DsbA, or the fusion protein has one or more additional domains for example, such as a cellulose-binding domain, green fluorescent protein, maltose-binding protein, calmodulin-binding protein, glutathione S-transferase or lacZ.

In a further embodiment the invention relates to an assay, for example a multiplex assay, a bead-based assay, or protein array for identifying and characterising a substance, for example a hit, a lead substance, or an active substance for SSc. Here, a substance to be analysed is used. This can be any native or non-native biomolecule, a (synthetic) chemical molecule, a natural substance, a mixture or a substance library. Once the substance to be analysed has contacted an SSc marker, the binding success is evaluated, for example using commercially available image analysis software (GenePix Pro (Axon Laboratories), Aida (Raytest), or ScanArray (Packard Bioscience).

Binding according to the invention, binding success, interactions, for example protein-protein interactions (for example protein to SSc marker, such as antigen/antibody) or corresponding "means for detecting the binding success" can be visualised, for example, by means of fluorescence labelling, biotinylation, radio-isotope labelling or colloidal gold or latex particle labelling in the conventional manner. Bound antibodies are preferably detected with the aid of secondary antibodies, which are labelled with commercially available reporter molecules (for example Cy, Alexa, Dyomics, FITC or similar fluorescent dyes, colloidal gold or latex particles), or with reporter enzymes, such as alkaline phosphatase, horseradish peroxidase, etc. and the corresponding colorimetric, fluorescent or chemoluminescent substrates. A readout is performed visually, for example.

The following examples explain the invention, but do not limit the invention to the examples. In the following figures, systemic sclerosis is denoted by PPS (progressive systemic sclerosis).

The patent or application file contains at least one drawing executed in color. Copies of this patent or patent application publication with color drawing(s) will be provided by the Office upon request and payment of the necessary fee.

EXAMPLES

Figure 1:
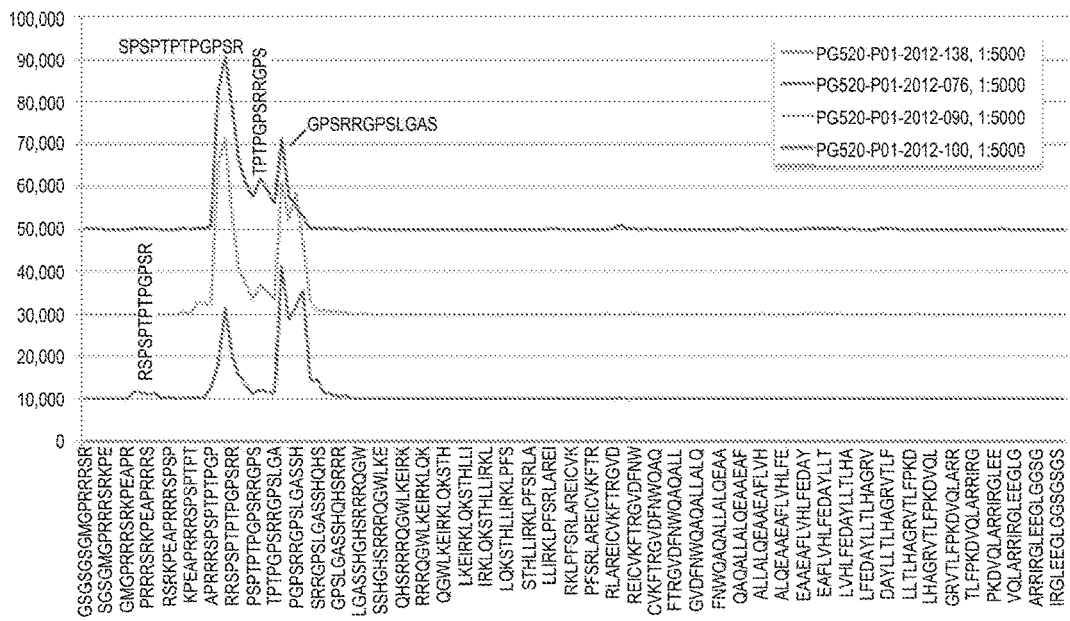
FIG. 1 shows the intensity plots of the CENPA peptides that were achieved with the patient samples PG520-P01-2012-076, PG520-P01-2012-090, PG520-P01-2012-100 and PG520-P01-2012-138 at a dilution of 1:5000.
Figure 2:
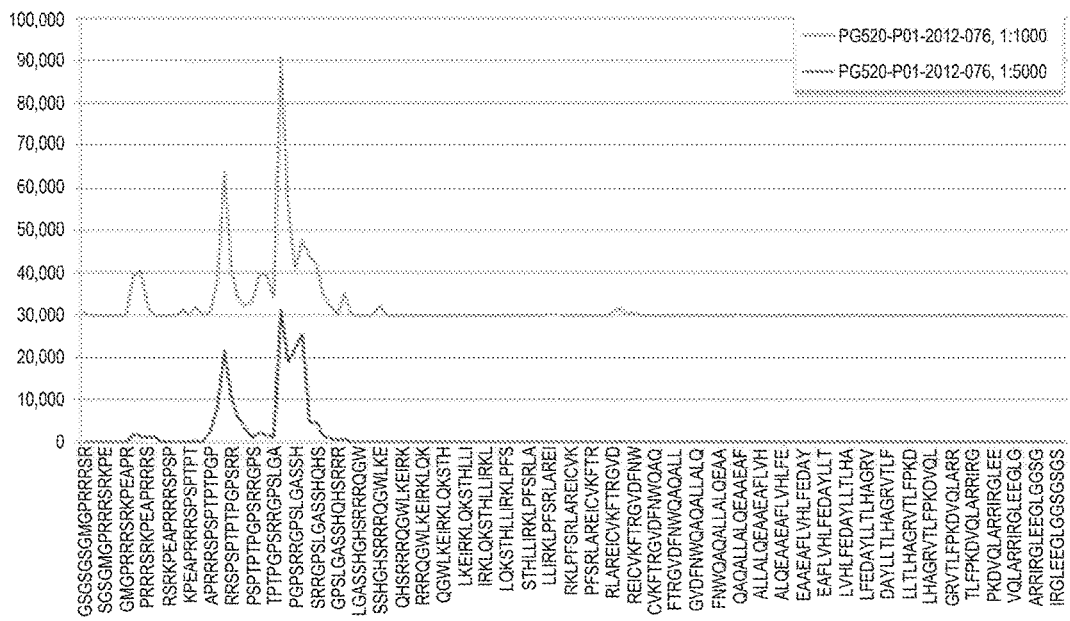
FIG. 2 shows the intensity plots of the CENPA peptides that were achieved with the patient sample PG520-P01-2012-076.

Example 1: Description and Objective of the Study

The objective of the study was to determine the relevant epitope/the relevant epitopes of the novel autoantigen KDM6B. Within the scope of this study, peptide microarrays from PEPperPRINT (http://www.PEPperPRINT.com) were used.

The CENPA antigen was analysed as the target antigen and used for the evaluation of the technology. In addition, the novel KDM6B antigen was used as an antigen for the diagnosis of SSc. While this antigen originally has a very large scope, it was only expressed as a short N-terminal fragment.

For epitope mapping, 15-mer peptides were generated, with an overlap of 14 amino acids from peptide to peptide.

All peptides that cover the sequence of both antigens were printed on a flat microarray by way of PEPperPRINT. In total, four microarrays were generated. For analysis, three sera from SSc patients which exhibited reactivity to both antigens were selected and incubated on the arrays. One serum from an SSc patient which exhibited no reactivity to these two antigens was used as the negative control.

The primary objective of the present study was to identify the relevant immunogenic regions/epitopes of CENPA, labelled by SSc sera, by way of peptide microarrays, and to compare the results to the previously published state of the art.

The secondary objective of the present study was to identify putative immunogenic epitopes of a novel antigen (KDM6B).

The third objective was to analyse whether the three disease sera behave identically or whether they exhibit biological diversity based on polyclonal immune response.

Example 2: Selection of the SSc Patient and Control Samples

In total, four different samples from SSc patients were selected on the basis of the reactivity thereof to the respective antigens CENPA and KDM6B (Table 1).

Three of the SSc patient samples (PG520-P01-2012-076, PG520-P01-2012-090, PG520-P01-2012-100), which tested positive for anti-CENPA and anti-KDM6B protein fragments, were selected as positive samples.

An SSc control sample (PG520-P01-2012-138), which showed negative test results for anti-CENPA and anti-KDM6B, was included. However, this does not preclude the possibility that this sample may react negatively to an epitope located at a distance from the region that was tested in the previous screen.

TABLE 1

Overview of positive and negative control series/plasma samples that were incubated on peptide arrays.

| Tube Barcode | Sample Identifier | Group | Gender | Indication | Diagnose | Antiz + | SCL 70+ | Ana pos | Age of donor | Sample external identifier | Donor identifier |
|---|---|---|---|---|---|---|---|---|---|---|---|
| 116654445 | PG520-P01-2012-090 | PSS | F | Progressive | diffuse F. | X | — | X | 52 | 21 | PG520-P01-2012-090D |
| 116654423 | PG520-P01-2012-076 | PSS | F | Progressive | limitierte F. | X | — | X | 553 | 7 | PG520-P01-2012-076D |
| 116654420 | PG520-P01-2012-100 | PSS | F | Progressive | limitierte F. | X | — | X | 557 | 31 | PG520-P01-2012-100D |
| 116654439 | PG520-P01-2012-076 | PSS | F | Progressive | limiterte F. | — | — | X | 553 | 69 | PG520-P01-2012-138D |

| | | Tube Barcode | Date of Birth | BBA16.344_0105510253 | BBA17.083_1047890025 | BBA25.203_1066859716 | BBA16.344_0105510253 | BBA17.083_1047890025 | BBA25.203_1066859716 |
|---|---|---|---|---|---|---|---|---|---|
| | | | GeneID | 23135 | 23135 | 1058 | 23135 | 23135 | 1058 |
| | | | Gene Symbol | KDM6B | KDM6B | CENPA | KDM6B | KDM6B | CENPA |
| | | | Gene Name | lysine (K)-specific demethylase 6B | lysine (K)-specific demethylase 6B | centromere protein A | lysine (K)-specific demethylase 6B | lysine (K)-specific demethylase 6B | centromere protein A |
| | | | HV Mean | 776 | 2108 | 1760 | 458 | 1191 | 925 |
| | | | HVSD | 991 | 2563 | 3822 | 914 | 3064 | 1829 |
| | | | | SLE | SLE | SLE | HV | HV | HV |
| | | | Cutoff mean + 2 SD | 2757.7321 | 7234.02335 | 9404.01883 | 2286 | 7319 | 4583 |
| | | | Cutoff mean + 2 SD | 2758 | 7234 | 9404 | 2286 | 7319 | 4583 |
| | | | Cutoff mean + 3 SD | 3749 | 9797 | 13226 | 3200 | 10383 | 6411 |
| | | 116654445 | NA | 18576.4937 | 49161.9785 | 17368.5453 | 18576 | 49162 | 17369 |
| | | 116654423 | NA | 29769.6421 | 49161.9785 | 27676.8844 | 29770 | 49162 | 27677 |
| | | 116654420 | NA | 10340.0046 | 17180.4974 | 27676.8844 | 10340 | 17180 | 27677 |
| | | 116654439 | NA | 368 | 878 | 206 | 368 | 878 | 206 |

Example 3: Epitope Mapping by Way of Peptide Microarrays 3.1 Description of Peptide Microarrays The antigens CENPA and KDM6B were converted into 15-mer peptides with an overlap between peptides of 14 amino acids, which resulted in 1,831 different peptides, printed in duplicates (a total of 3,662 peptide spots). The corresponding peptide microarrays were additionally framed by FLAG and HA control peptides (124 spots each).

3.2 Experimental Conditions and Procedure

The experimental conditions were listed as indicated by PEPperPRINT:

Incubation buffer: PBS, pH 7.4 with 0.05% Tween 20 and 10% Rockland's blocking buffer Washing buffer: PBS, pH 7.4 with 0.05% Tween 20 (2×1 min after each assay)

Blocking buffer: Rockland's blocking buffer MB-070 (60 min prior to first assay)

Conditions for the assay: serum dilutions of 1:5000 and 1:1000 in the incubation buffer; incubation for 16 hrs at 4° C. and shaking at 500 rpm.

Secondary antibody: F(ab')2 goat anti-human IgG(H+L) conj. DyLight680; 30 min staining at RT and a dilution of 1:5000

Control antibody: monoclonal anti-HA (12CA5)-DyLight680, monoclonal anti-FLAG(M2)-DyLight800; staining in the incubation buffer for 1 h at RT and a dilution of 1:1000

Scanner: LI-COR Odyssey Imaging System; scanning offset 1 mm, resolution 21 µm, scanning intensity green/red 7/7

Microarray data: MicroarrayData_PG520-P01-2012-076.xlsx, MicroarrayData_PG520-P01-2012-090.xlsx, MicroarrayData_PG520-P01-2012-100.xlsx, Microarray-Data_PG520-P01-2012-138.xlsx, MircoarrayData_Summary.xlsx Microarray identification: 000616_02, 000616_03, 000646_05, 000646_06 (two array copies per microarray)

The pre-staining of one of the peptide arrays was carried out with the F(ab')2 goat anti-human IgG(H+L) conj. DyLight680 antibody at a dilution of 1:5000 to analyse the background interactions with the peptides that included no antigens, which could impair the primary assays. The subsequent incubation of the peptide microarrays with the human sera PG520-P01-2012-076, PG520-P01-2012-090, PG520-P01-2012-100 and PG520-P01-2012-138 at dilutions of 1:5000 and 1:1000 in the incubation buffer was followed by staining with the secondary antibody and the readout at a scanning intensity of 7 (red). HA and FLAG control peptides, which frame the peptide arrays, were finally stained for internal quality control to verify the quality of the assay and the integrity of the peptide microarray (scanning intensities red/green 7/7).

Example 4: Data Analysis

The data analysis was carried out by way of PEPperPRINT as described hereafter. The quantification of the spot intensities and the peptide detection were carried out with the aid of the PepSlide® analyser. A software algorithm breaks down the fluorescence intensities of every spot into raw, foreground and background signals and calculates the standard deviation from mean foreground intensities. Intensity maps were generated based on averaged mean foreground intensities, and the binders were labeled in the peptide maps by a red intensity color code for high spot intensities and in white for low spot intensities.

PEPperPRINT additionally recorded averaged spot intensities of all assays against the linked antigen sequences from the N-terminus of CENPA to the C-terminus of KDM6B so as to visually represent all the spot intensities and the relationship between signal and sound.

The intensity plots were correlated with peptide and intensity maps and with a visual inspection of the microarray scans so as to identify peptides and consensus patterns that interacted with the plasma samples.

Where it was unclear whether a certain amino acid contributed to the binding of antibodies, the corresponding letters were written in gray color.

Example 5: Peptide Mapping of CENPA

As shown in FIG. 1, the intensity plots (dilution 1:5000) of the CENPA peptides underscored the very strong and almost identical reaction of the sera PG520-P01-2012-076, PG520-P01-2012-090 and PG520-P01-2012-100 with the two primary epitopes RSPSPTPTPGPSR (SEQ ID No. 13) and GPSRRGPSLGAS (SEQ ID No. 11) and a third, but superimposed (overlapping) epitope TPTPGPSRRGPS (SEQ ID No. 12).

Figure 3:
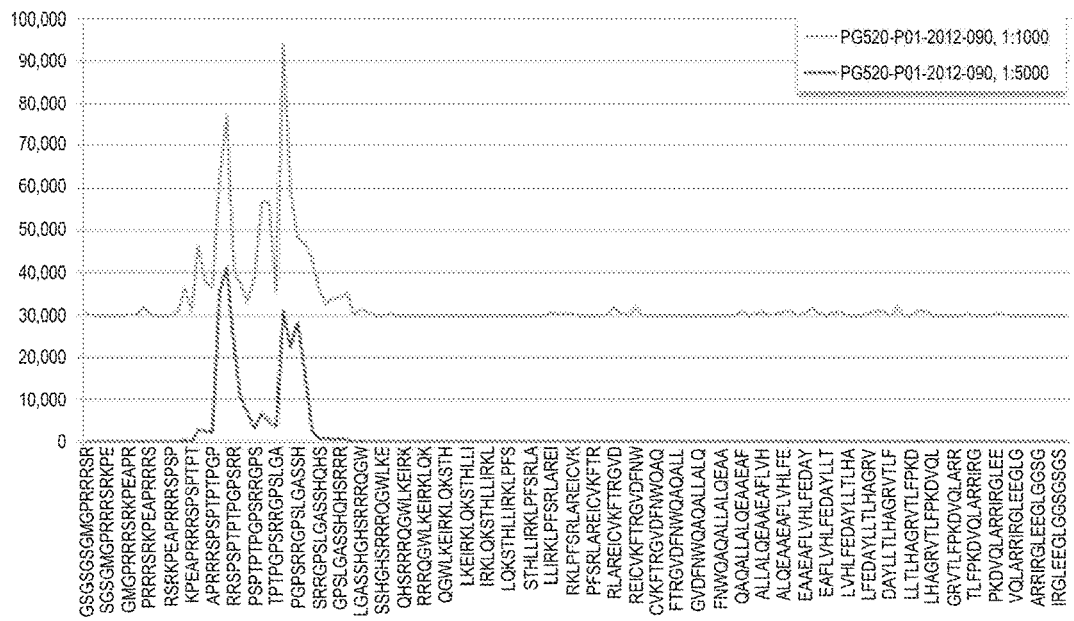
FIG. 3 shows the intensity plots of the CENPA peptides that were achieved with the patient sample PG520-P01-2012-090.
Figure 4:
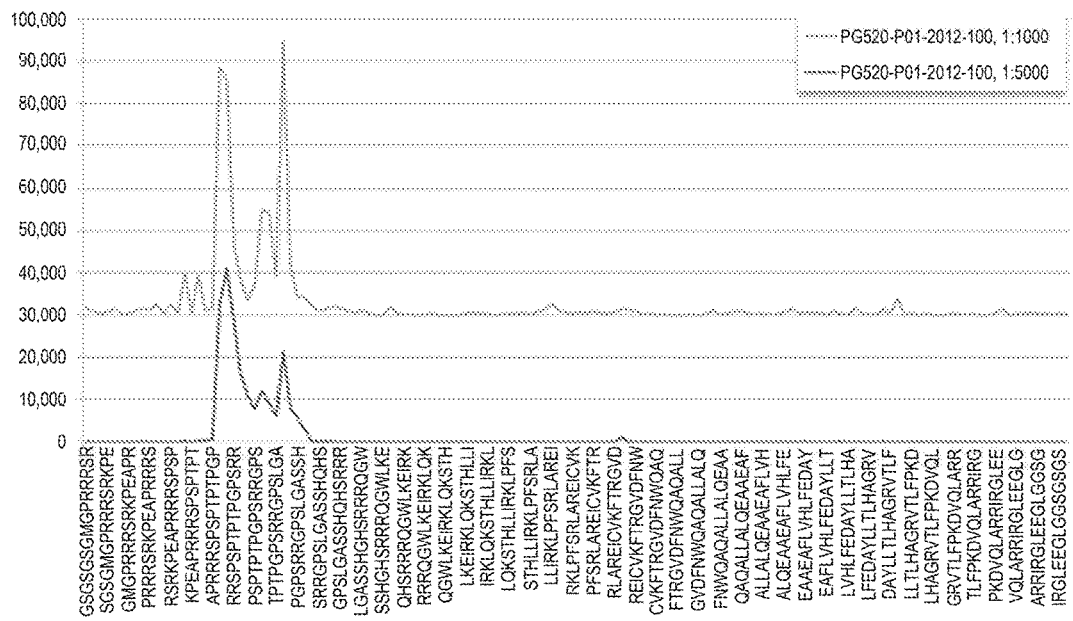
FIG. 4 shows the intensity plots of the CENPA peptides that were achieved with the patient sample PG520-P01-2012-100.

All these three individual peptides are represented by the amino acids (aa) 16-36 (FIG. 1). The serum PG520-P01-2012-076 showed a minor difference in the intensity ratio of the two primary epitopes and caused an additional N-terminus epitope RSPSPTPTPGPSR (SEQ ID No. 15) or PRRRSRKPEAPR (SEQ ID No. 14)(represented by aa 3-14). This epitope also has a weak reaction in the sample PG520-P01-2012-090 at a dilution of 1:1000 (FIG. 3). Moreover, the sample PG520-P01-2012-100 exhibits an additional reaction to this N-terminus region at a dilution of 1:1000 (FIG. 4).

Figure 5:
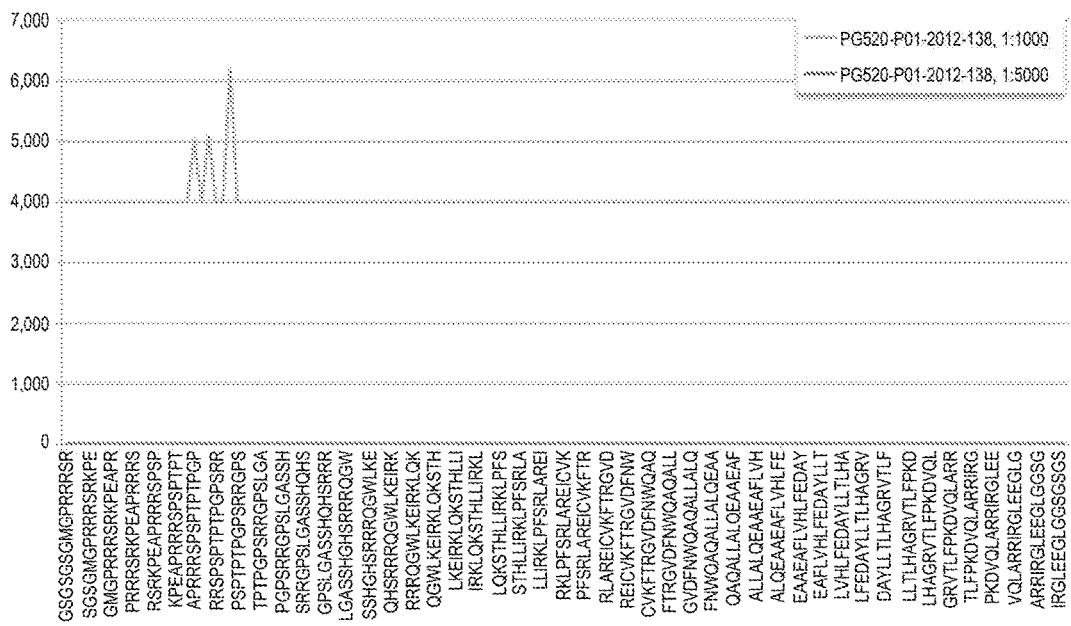
FIG. 5 shows the intensity plots of the CENPA peptides that were achieved with the patient sample PG520-P01-2012-138.

The patient sample PG520-P01-2012-138, which tested negative for anti-CENPA in the Luminex Perl assay, exhibits a weak reaction (FIG. 5). Only three individual peptide interactions based on the peptides APRRRSPSPTPTPGP (SEQ ID No. 16), RRRSPSPTPTPGPSR (SEQ ID No. 17) and SPSPTPTPGPSRRGP (SEQ ID No. 18) were observed at a dilution of 1:1000, not, however, at a dilution of 1:5000.

Example 6: Distribution of the Epitopes of CENPA

The distribution of the epitopes that were identified by way of peptide mapping is shown in Table 2.

TABLE 2

| The amino acid sequence of CENPA (Gen ID: 1058) |
|---|
| MGPRRRSRKPEAPRRSPSPTPTPGPSRRGPSLGASSHQHSRRRQGWLKEIRKLQKSTHLLI |
| RKLPFSRLAREICVKFTRGVDFNWQAQALLALQEAAEAFLVHLFEDAYLLTLHAGRVTLFPK |
| DVQLARRIRGLEEGLG |

The larger epitope identified by peptide mapping is double-underlined (aa 16-36), while the second, weaker epitope is single-underlined (aa 3-14).

Muro et al. expressed a series of cut peptides in *E. coli* and conducted an immunoblot analysis with 91 ACA-positive sera (Muro et. al., 2000). Eighty of the sera (88%) with ACA reacted to the N-terminus region with 52 amino acids, while none of the sera reacted to the C-terminus. Two synthetic peptides (amino acid sequences aa 3±17 (peptide A) and as 25±38 (peptide B)) reacted in ELISA to 78 (86%) and 79 (87%) of the ACA-positive sera. Peptide A corresponds to the second epitope (aa 3-14), which was less reactive in our presently tested patient samples than described by Muro et al. (2000). Peptide B is part of the larger epitope (aa 16-36) identified by peptide arrays.

By way of the systematic approach of peptide mapping, it is possible to identify not only individual epitopes in the order of magnitude of the presently used peptides (14 aa), but also larger regions that are covered by multiple, overlapping peptides.

TABLE 3

DNA sequence of Homo sapiens centromere protein A
(CENPA), transcription variant 1, mRNA (ref|NM_001809.31)

```
1     ccgtgaagtg ggcggagcga gcgatttgaa cgcgagcggc gcggact-
tct gccaagcacc 61    ggctcatgtg aggctcgcgg cacagcgttc tctgggctcc cca-
gaagcca gcctttcgct 121   cccggacccg gcagcccgag caggagccgt gggaccgggc gccagcaccc tctgcg-
gcgt 181   gtcatgggc                                        aggcg cagc-
ccgagc 241   ccgaccccga cccccggccc ctcccggcgg ggccctcct taggcgcttc ctcccat-
caa 301   cacagtcggc ggagacaagg ttggctaaag gagatccgaa agcttcagaa gagcaca-
cac 361   ctcttgataa ggaagctgcc cttcagccgc ctggcaagag aaatatgtgt taaat-
tcact 421   cgtggtgtgg acttcaattg gcaagcccag gccctattgg ccctacaaga ggcagca-
gaa 481   gcatttctag ttcatctctt tgaggacgcc tatctcctca ccttacatgc agac-
cgagtt 541   actctcttcc caaaggatgt gcaactgacc cggaggatcc ggggcct-
tga ggagggactc 601   ggctgagctc ctgcacccag tgtttctgtc agtctttcct gctcagccag ggggat-
gat 661   accggggact ctccagagcc atgactagat ccaatggatt ctgcgatgct gtctg-
gactt 721   tgctgtctct gaacagtatg tgtgtgttgc tttaaat-
att tttcttttt ttgagaagga 781   gaagactgca tgactttcct ctgtaacaga ggtaatatat gagacaatca acaccgt-
tcc 841   aaaggcctga aaataatttt cagataaaga gactccaagg ttgactttag tttgt-
gagtt 901   actcatgtga ctatttgagg attttgaaaa catcagattt gctgtggtat ggga-
gaaaag 961   gctatgtact tattatttta gctctttctg taatatttac attttttacc atatgta-
cat 1021  ttgtacttt attttacaca taagggaaaa aataagacca ctttgagcag ttgcctg-
gaa 1081  ggctgggcat ttccatcata tagacctctg cccttcagag tagcctcacc attagtg-
gca 1141  gcatcatgta actgagtgga ctgtgcttgt caacggatgt gtagcttttc agaaact-
taa 1201  ttggggatga atagaaaacc tgtaagcttt gatgttctgg ttacttctag taaattc-
ctg 1261  tcaaaatcaa ttcagaaatt ctaacttgga gaatttaaca ttttactctt gtaaat-
cata
```

TABLE 3-continued

DNA sequence of Homo sapiens centromere protein A (CENPA), transcription variant 1, mRNA (ref|NM_001809.31)

```
1321 gaagatgtat cataacagtt cagaatttta aagtacattt tcgatgcttt tatgggtatt 1381 tttgtagttt ctttgtagag agataataaa aatcaaaata tttaatgaaa a
``` gray: coding sequence (base pair 184-606);
blue: sequence of the expression clone 00700_007_E24, BBA25_203;
red: the larger epitope identified by peptide mapping;
black: sequence portions not represented by the expression clone.

Example 6: Peptide Mapping of KDM6B

Figure 6:
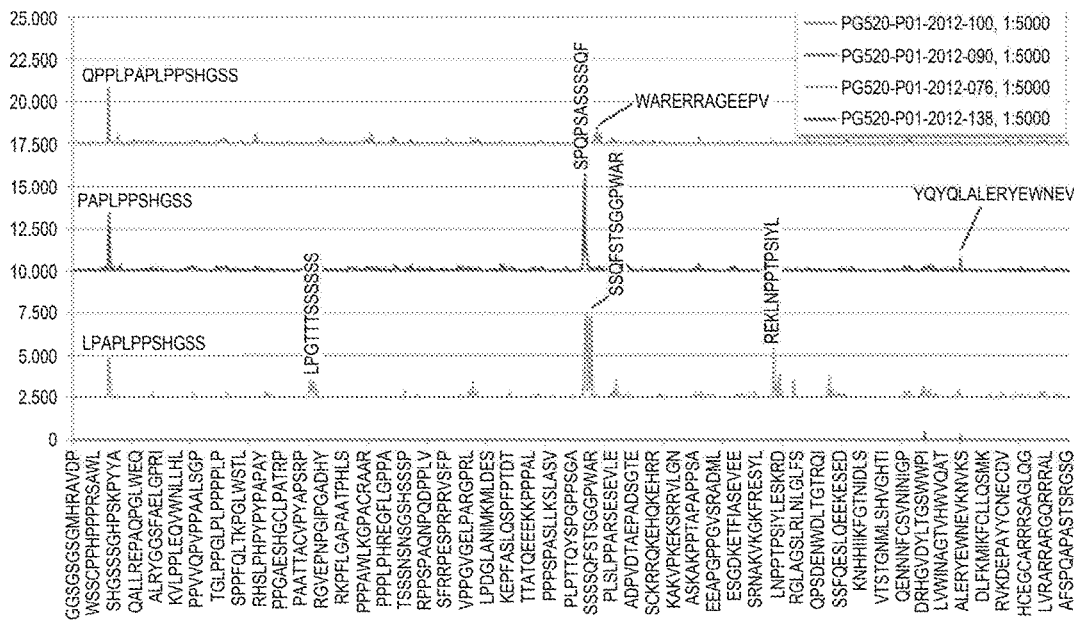
FIG. 6 shows the intensity plots of the KDM6B peptides that were achieved with the patient samples PG520-P01-2012-076, PG520-P01-2012-090, PG520-P01-2012-100 and PG520-P01-2012-138 at a dilution of 1:5000.

As shown in FIG. 6, the intensity plots (dilution 1:5000) underscored the moderate to strong and partially similar reaction of the sera PG520-P01-2012-076, PG520-P01-2012-090 and PG520-P01-2012-100 with the primary epitopes LPAPLPPSHGSS (SEQ ID No. 2) and SPQPSASSSSQF (SEQ ID No. 3). The LPAPLPPSHGSS epitope (SEQ ID No. 2) (aa 55-67) was common to all positive serum samples.

In contrast, the SPQPSASSSSQF ((SEQ ID No. 3) as 861-873) epitope was only observed in the sera PG520-P01-2012-076 and PG520-P01-2012-090. The neighboring epitope SSQFSTSGGPWAR (SEQ ID No. 4) (aa 870-881), however, was likewise detected in sample PG520-P01-2012-076 and GGPWARERRAGEEPV (SEQ ID No. 6)(aa 877-890) and was detected slightly by PG520-P01-2012-100 (1:1000 dilution). The result is an immunogenic region from aa 861 to aa 890.

Other epitopes, such as REKLNPPTPSIYL (SEQ ID No. 5), were identified only in one of the samples.

Figure 7:
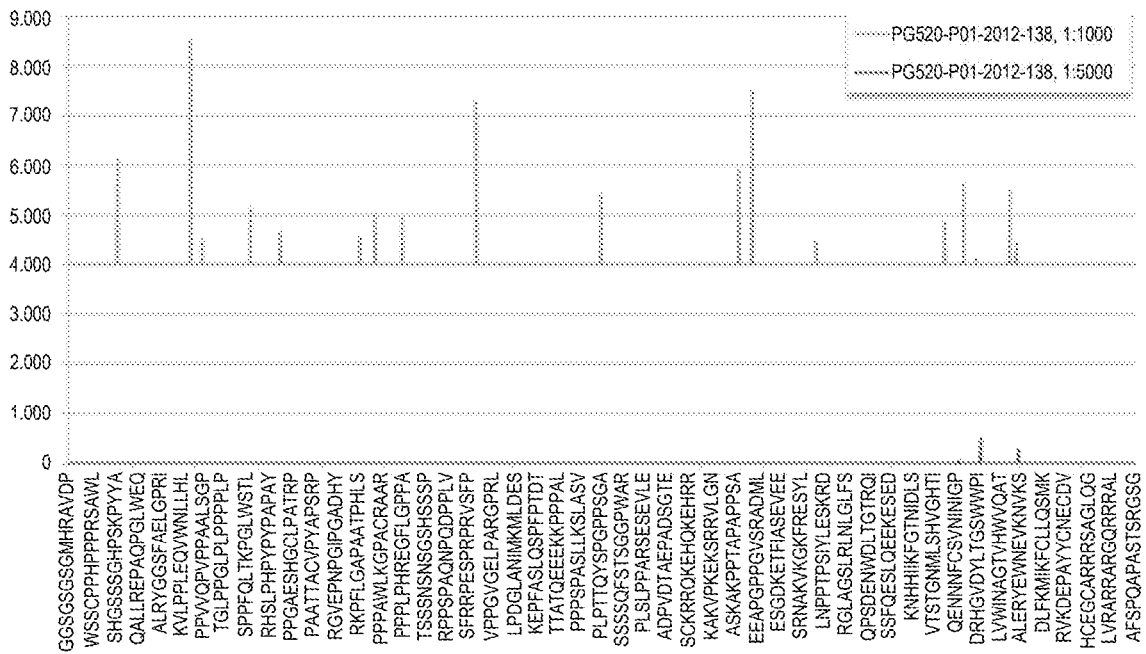
FIG. 7 shows the intensity plots of the KDM6B peptides that were achieved with the patient sample PG520-P01-2012-138.

The patient sample PG520-P01-2012-138, which tested negative for KDM6B in the Luminex Perl assay, exhibited a weak to moderate reaction to several individual peptides at a dilution of 1:1000, and to two different peptides at a dilution of 1:5000. The majority of interactions were either based on highly alkaline peptides such as KRNYGAKRG-GPPVKR (SEQ ID No. 19) or hydrophobic peptides comprising a proline at the C-terminus (such as FPKTPEVG-PGPPPGP (SEQ ID No. 20) or GIPSKPYYAPGAPTP (SEQ ID No. 21). Given the indistinct morphology of the spots, the weak spot intensities and the general inconsistency of the data, all interactions were rated to be non-specific (FIG. 7).

Example 7: Distribution of the Epitopes of KDM6B and Representation of KDM6B in the Sero Tag The distribution of the epitopes that were identified by way of peptide mapping is shown in Table 4. In the Sero-Tag Discovery Screens, three clones express KDM6B antigen (or fragments of KDM6B). All three expression clones express a similar coding region (aa 42-435) and comprise the largest LPAPLPPSHGSS (SEQ ID No. 2) epitope.

A second immunogenic region, which is covered by >3 peptides (aa 861-890), is not represented by these expression clones. The combination of the two immunogenic epitopes/regions will improve the detection of KDM6B-positive samples.

The epitope mapping of KDM6B results in two larger epitopes and only one epitope that was detected in one of three KDM6B-positive samples. All three available expression clones of KDM6B express the similar code region (aa 42-435) and comprise the one of the larger epitopes (LPA-PLPPSHGSS, SEQ ID No. 2). The second immunogenic region, which is covered by >3 peptides (aa 861-890), is not represented by these expression clones.

TABLE 4

The amino acid sequence of KDM6B (Gen ID: 23135) The larger epitope identified by way of peptide mapping is shown in bold and underlined (aa 55-67), while the second region is composed of > peptides and double-underlined (aa 861-890). A third epitope, which was detected in only one sample, is single-underlined. Bold: expressed sequence using expression clones in the Sero tag.

MHRAVDPPGARAAREAFALGGLSCAGAWSSCPPHPPPRSAWLPGGRCSASIGQPPLPAPLPP

SHGSSSGHPSKPYYAPGAPTPRPLHGKLESLHGCVQALLREPAQPGLWEQLGQLYESEHDSE

EATRCYHSALRYGGSFAELGPRIGRLQQAQLWNFHTGSCQHRAKVLPPLEQVWNLLHLEHKR

NYGAKRGGPPVKRAAEPPVVQPVPPAALSGPSGEEGLSPGGKRRRGCNSEQTGLPPGLPLPP

PPLPPPPPPPPPPPPLPGLATSPPFQLTKPGLWSTLHGDAWGPERKGSAPPERQEQRHSLP

HPYPYPAPAYTAHPPGHRLVPAAPPGPGPRPPGAESHGCLPATRPPGSDLRESRVQRSRMDS

SVSPAATTACVPYAPSRPPGLPGTTTSSSSSSSSNTGLRGVEPNPGIPGADHYQTPALEVS

HHGRLGPSAHSSRKPFLGAPAATPHLSLPPGPSSPPPPPCPRLLRPPPPPAWLKGPACRAAR

EDGEILEELFFGTEGPPRPAPPPLPHREGFLGPPASRFSVGTQDSHTPPTPPTPTTSSSNSN

TABLE 4-continued

The amino acid sequence of KDM6B (Gen ID: 23135) The larger epitope identified by way of peptide mapping is shown in bold and underlined (aa 55-67), while the second region is composed of > peptides and double-underlined (aa 861-890). A third epitope, which was detected in only one sample, is single-underlined. Bold: expressed sequence using expression clones in the Sero tag.

SGSHSSSPAGPVSFPPPPYLARSIDPLPRPPSPAQNPQDPPLVPLTLALPPAPPSSCHQNTS

GSFRRPESPRPRVSFPKTPEVGPGPPPGPLSKAPQPVPPGVGELPARGPRLFDFPPTPLEDQ

FEEPAEFKILPDGLANIMKMLDESIRKEEEQQQHEAGVAPQPPLKEPFASLQSPFPTDTAPT

TTAPAVAVTTTTTTTTTTTATQEEEKKPPPALPPPPPLAKFPPPSQPQPPPPPPPSPASLLK

SLASVLEGQKYCYRGTGAAVSTRPGPLPTTQYSPGPPSGATALPPTSAAPSAQG<u>SPQPSASS</u>

<u>SSQFSTSGGPWARERRAGEEPV</u>PGPMTPTQPPPPLSLPPARSESEVLEEISRACETLVERVG

RSATDPADPVDTAEPADSGTERLLPPAQAKEEAGGVAAVSGSCKRRQKEHQKEHRRHRRACK

DSVGRRPREGRAKAKAKVPKEKSRRVLGNLDLQSEEIQGREKSRPDLGGASKAKPPTAPAPP

SAPAPSAQPTPPSASVPGKKAREEAPGPPGVSRADMLKLRSLSEGPPKELKIRLIKVESGDK

ETFIASEVEERRLRMADLTISHCAADVVRASRNAKVKGKFRESYLSPAQSVKPKINTEEKL<u>P</u>

<u>REKLNPPTPSIYLE</u>SKRDAFSPVLLQFCTDPRNPITVIRGLAGSLRLNLGLFSTKTINEASG

EHTVEVRTQVQQPSDENWDLTGTRQIWPCESSRSHTTIAKYAQYQASSFQESLQEEKESEDE

ESEEPDSTTGTPPSSAPDPKNHHIIKFGTNIDLSDAKRWKPQLQELLKLPAFMRVTSTGNML

SHVGHTILGMNTVQLYMKVPGSRTPGHQENNNFCSVNINIGPGDCEWFAVHEHYWETISAFC

DRHGVDYLTGSWWPILDDLYASNIPVYRFVQRPGDLVWINAGTVHWVQATGWCNNIAWNVGP

LTAYQYQLALERYEWNEVKNVKSIVPMIHVSWNVARTVKISDPDLFKMIKFCLLQSMKHCQV

QRESLVRAGKKIAYQGRVKDEPAYYCNECDVEVFNILFVTSENGSRNTYLVHCEGCARRRSA

GLQGVVVLEQYRTEELAQAYDAFTLVRARRARGQRRRALGQAAGTGFGSPAAPFPEPPPAFS

PQAPASTSR

LITERATURE

Mehra S, Walker J, Patterson K, Fritzler M J (2013). Autoantibodies in systemic sclerosis. Autoimmun Rev. 12(3):340-54.

Mierau R, Moinzadeh P, Riemekasten G, Meichers I, Meurer M, Reichenberger F, Buslau M, Worm M, Blank N, Hein R, Müller-Ladner U, Kuhn A, Sunderkötter C, Juche A, Pfeiffer C, Fiehn C, Sticherling M, Lehmann P, Stadler R, Schuize-Lohoff E, Seitz C, Foeldvari I, Krieg T, Genth E, Hunzelmann N (2011). Frequency of disease-associated and other nuclear autoantibodies in patients of the German Network for Systemic Scleroderma: correlation with characteristic clinical features. Arthritis Res Ther. 13(5): R172

LeRoy E C, Black C, Fleischmajer R, Jablonska S, Krieg T, Medsger T A Jr, Rowell N, Wollheim F (1988). Scleroderma (systemic sclerosis): classification, subsets and pathogenesis. J Rheumatol. 15(2):202-5.

Watts R., (2006). Autoantibodies in the autoimmune rheumatic diseases, Medicine, 34 (11): 441-444

The invention claimed is:

1. A panel of markers for use with systemic sclerosis (SSc), comprising at least two different markers attached to a solid substrate, wherein each of the markers have a peptide sequence selected independently of one another from any one of SEQ ID NOs: 1-10, 13 and 15-18.

2. The panel of claim 1, wherein at least one of the markers has a length of no more than 25 amino acids.

3. The panel of claim 1, wherein at least one of the markers has a length of no more than 15 amino acids.

4. The panel of claim 1, wherein the markers comprise a binding region.

5. The panel of claim 1, wherein the markers comprise an epitope.

6. A diagnostic device or a test kit for use with SSc, comprising
a panel of markers comprising at least two different markers attached to a solid substrate, wherein each of the markers have a peptide sequence selected independently of one another from the peptide sequences of SEQ ID NO: 1-10, 13, and 15-18.

7. A composition comprising at least one marker from the panel of markers of claim 1.

8. The composition of claim 7, wherein the composition is a pharmaceutical composition for specific application in SSc.

9. The panel of claim 1, wherein the markers have the peptide sequences selected independently from any one of SEQ ID NOs: 1, 3, 4, and 6.

10. The panel of claim 1, wherein the markers bind to autoantibodies that are present during the course of development, establishment, or therapy of SSc.

11. The panel of claim 10, wherein the markers bind to autoantibodies that are up-regulated or down-regulated during the course of development, establishment, or therapy of SSc.

* * * * *